US011246717B2

(12) United States Patent
Aghayev et al.

(10) Patent No.: US 11,246,717 B2
(45) Date of Patent: Feb. 15, 2022

(54) EXPANDABLE INTERVERTEBRAL CAGE

(71) Applicants: H. LEE MOFFITT CANCER CENTER AND RESEARCH INSTITUTE, INC., Tampa, FL (US); University of South Florida, Tampa, FL (US)

(72) Inventors: Kamran Aghayev, Tampa, FL (US); James J. Doulgeris, Oldsmar, FL (US); Sabrina A. Gonzalez Blohm, Tampa, FL (US); Frank D. Vrionis, Tampa, FL (US)

(73) Assignees: H. LEE MOFFITT CANCER CENTER AND RESEARCH INSTITUTE, INC., Tampa, FL (US); University of South Florida, Tampa, FL (US)

( * ) Notice: Subject to any disclaimer, the term of this patent is extended or adjusted under 35 U.S.C. 154(b) by 47 days.

(21) Appl. No.: 16/443,302

(22) Filed: Jun. 17, 2019

(65) Prior Publication Data
US 2019/0298540 A1    Oct. 3, 2019

Related U.S. Application Data

(63) Continuation of application No. 15/500,969, filed as application No. PCT/US2015/043109 on Jul. 31, 2015, now Pat. No. 10,322,009.

(60) Provisional application No. 62/031,955, filed on Aug. 1, 2014.

(51) Int. Cl.
*A61F 2/44* (2006.01)
*A61F 2/30* (2006.01)

(52) U.S. Cl.
CPC ............ *A61F 2/447* (2013.01); *A61F 2/4455* (2013.01); *A61F 2002/305* (2013.01); *A61F 2002/3055* (2013.01); *A61F 2002/30168* (2013.01); *A61F 2002/30171* (2013.01); *A61F 2002/30261* (2013.01); *A61F 2002/30383* (2013.01); *A61F 2002/30398* (2013.01); *A61F 2002/30405* (2013.01); *A61F 2002/30525* (2013.01); *A61F 2002/30545* (2013.01); *A61F 2002/30556* (2013.01); *A61F 2002/30565* (2013.01); *A61F 2002/30571* (2013.01);
(Continued)

(58) Field of Classification Search
CPC ................................................. A61F 2/44-447
See application file for complete search history.

(56) References Cited

U.S. PATENT DOCUMENTS

| 4,456,005 A | 6/1984 | Lichty |
| 4,858,601 A | 8/1989 | Glisson |
| 5,171,278 A | 12/1992 | Pisharodi |

(Continued)

FOREIGN PATENT DOCUMENTS

WO    2013052807 A2    4/2013

OTHER PUBLICATIONS

International Preliminary Report on Patentability and Written Opinion for PCT/US2015/043109, dated Feb. 16, 2016.
(Continued)

*Primary Examiner* — Nicholas J Plionis
(74) *Attorney, Agent, or Firm* — Meunier Carlin & Curfman LLC

(57) ABSTRACT

A method and system for performing bone fusion and/or securing one or more bones, such as adjacent vertebra, are disclosed.

20 Claims, 33 Drawing Sheets

(52) U.S. Cl.
CPC ........... *A61F 2002/30579* (2013.01); *A61F 2002/30836* (2013.01); *A61F 2002/30904* (2013.01)

(56) References Cited

U.S. PATENT DOCUMENTS

| | | | |
|---|---|---|---|
| 5,609,635 | A | 3/1997 | Michelson |
| 6,039,761 | A | 3/2000 | Li et al. |
| 6,517,543 | B1 | 2/2003 | Berrevoets et al. |
| 6,821,298 | B1 | 11/2004 | Jackson |
| 6,921,403 | B2 | 7/2005 | Cragg et al. |
| 7,217,293 | B2 | 5/2007 | Branch, Jr. |
| 7,799,057 | B2 | 9/2010 | Hudgins et al. |
| 7,879,098 | B1 | 2/2011 | Simmons, Jr. |
| 8,043,334 | B2 | 10/2011 | Fisher et al. |
| 9,351,848 | B2 | 5/2016 | Glerum et al. |
| 9,482,260 | B1 | 11/2016 | Krause |
| 9,566,168 | B2 | 2/2017 | Glerum et al. |
| 9,820,788 | B2 | 11/2017 | Vrionis et al. |
| 10,105,238 | B2 | 10/2018 | Koch et al. |
| 10,314,631 | B2 | 6/2019 | Vrionis et al. |
| 10,322,009 | B2 | 6/2019 | Aghayev et al. |
| 10,390,963 | B2* | 8/2019 | Olmos ............. A61B 17/025 |
| 10,500,059 | B2 | 12/2019 | Grotz |
| 2002/0195827 | A1 | 12/2002 | Jackson et al. |
| 2004/0122431 | A1 | 6/2004 | Biedermann et al. |
| 2004/0210227 | A1 | 10/2004 | Trail et al. |
| 2005/0043735 | A1 | 2/2005 | Ahmad |
| 2005/0070911 | A1 | 3/2005 | Carrison et al. |
| 2005/0113917 | A1 | 5/2005 | Chae et al. |
| 2005/0143735 | A1 | 6/2005 | Kyle et al. |
| 2005/0197660 | A1 | 9/2005 | Haid et al. |
| 2005/0261683 | A1 | 11/2005 | Veldhuizen et al. |
| 2005/0261695 | A1 | 11/2005 | Cragg et al. |
| 2005/0277923 | A1 | 12/2005 | Sweeney et al. |
| 2006/0036322 | A1 | 2/2006 | Reiley et al. |
| 2006/0224241 | A1 | 10/2006 | Butler et al. |
| 2006/0287725 | A1* | 12/2006 | Miller ............. A61F 2/4455 623/17.11 |
| 2007/0167951 | A1 | 7/2007 | Ainsworth et al. |
| 2007/0270855 | A1 | 11/2007 | Partin et al. |
| 2009/0076607 | A1 | 3/2009 | Aalsma et al. |
| 2009/0118771 | A1 | 5/2009 | Gonzalez-hernandez |
| 2009/0254129 | A1 | 10/2009 | Tipirneni et al. |
| 2009/0281628 | A1 | 11/2009 | Oglaza et al. |
| 2010/0003638 | A1 | 1/2010 | Collins et al. |
| 2010/0036440 | A1 | 2/2010 | Morris et al. |
| 2010/0049244 | A1 | 2/2010 | Cohen et al. |
| 2010/0082109 | A1 | 4/2010 | Greenhalgh et al. |
| 2010/0285783 | A1 | 11/2010 | Huguet et al. |
| 2011/0034925 | A1 | 2/2011 | Tipirneni et al. |
| 2011/0035011 | A1* | 2/2011 | Cain ............. A61F 2/447 623/17.16 |
| 2011/0087294 | A1 | 4/2011 | Reiley et al. |
| 2011/0144703 | A1 | 6/2011 | Krause et al. |
| 2011/0224738 | A1 | 9/2011 | Sucec et al. |
| 2011/0301712 | A1* | 12/2011 | Palmatier ............. A61F 2/4611 623/17.16 |
| 2011/0319946 | A1 | 12/2011 | Levy et al. |
| 2012/0123546 | A1* | 5/2012 | Medina ............. A61F 2/447 623/17.16 |
| 2012/0209386 | A1* | 8/2012 | Triplett ............. A61F 2/447 623/17.16 |
| 2013/0006361 | A1 | 1/2013 | Glerum et al. |
| 2013/0053902 | A1 | 2/2013 | Trudeau et al. |
| 2013/0103156 | A1* | 4/2013 | Packer ............. A61F 2/447 623/17.16 |
| 2013/0190876 | A1* | 7/2013 | Drochner ............. A61F 2/442 623/17.16 |
| 2013/0190877 | A1 | 7/2013 | Medina |
| 2013/0211526 | A1 | 8/2013 | Alheidt et al. |
| 2013/0231747 | A1* | 9/2013 | Olmos ............. A61F 2/30771 623/17.16 |
| 2013/0325075 | A1 | 12/2013 | Jackson et al. |
| 2013/0325128 | A1 | 12/2013 | Perloff et al. |
| 2014/0012383 | A1 | 1/2014 | Triplett et al. |
| 2014/0052253 | A1* | 2/2014 | Perloff ............. A61F 2/4611 623/17.15 |
| 2014/0094916 | A1 | 4/2014 | Glerum et al. |
| 2014/0114312 | A1 | 4/2014 | Krause |
| 2014/0277139 | A1 | 9/2014 | Vrionis et al. |
| 2014/0277490 | A1* | 9/2014 | Perloff ............. A61F 2/4425 623/17.16 |
| 2015/0012048 | A1 | 1/2015 | Huebner et al. |
| 2015/0073552 | A1* | 3/2015 | To ............. A61F 2/4684 623/17.15 |
| 2016/0310190 | A1 | 10/2016 | Gonzalez Blohm et al. |
| 2016/0338846 | A1* | 11/2016 | Walker ............. A61F 2/4611 |
| 2017/0056200 | A1 | 3/2017 | Koch et al. |
| 2018/0014866 | A1 | 1/2018 | Vrionis et al. |
| 2018/0078384 | A1 | 3/2018 | Suddaby |
| 2018/0092677 | A1 | 4/2018 | Peterson et al. |
| 2018/0092751 | A1 | 4/2018 | Vrionis et al. |
| 2018/0071000 | A1 | 6/2018 | Pham et al. |
| 2018/0193164 | A1 | 7/2018 | Shoshtaev |
| 2019/0046328 | A1 | 2/2019 | Rosenwasser et al. |

OTHER PUBLICATIONS

International Search Report and Written Opinion for PCT/US2015/043109, dated Nov. 2, 2015.
International Search Report and Written Opinion for PCT/US2012/058968 dated Mar. 28, 2013.
International Preliminary Report on Patentability and Written Opinion for PCT/US2012/058968, dated Apr. 8, 2014.
International Search Report and Written Opinion for PCT/US2014/070899 dated May 14, 2015.
International Preliminary Report on Patentability and Written Opinion for PCT/US2014/070899 dated Jun. 21, 2016.
Co-Pending U.S. Appl. No. 15/718,786, filed Sep. 28, 2017.
Co-Pending U.S. Appl. No. 15/728,898, filed Oct. 10, 2017.
Co-Pending U.S. Appl. No. 15/970,204, filed May 3, 2018.
Co-Pending U.S. Appl. No. 15/970,212, filed May 3, 2018.
The prosecution history of U.S. Appl. No. 14/347,442, filed Mar. 26, 2014, issued as U.S. Pat. No. 9,820,788 on Nov. 21, 2017.
The prosecution history of U.S. Appl. No. 15/105,210, filed Jun. 16, 2016, issued as U.S. Pat. No. 10,314,631 on Jun. 11, 2019.
Office Action issued for U.S. Appl. No. 15/970,212, dated Sep. 24, 2020.
Notice of Allowance issued for U.S. Appl. No. 15/970,212, dated Jun. 3, 2021.

* cited by examiner

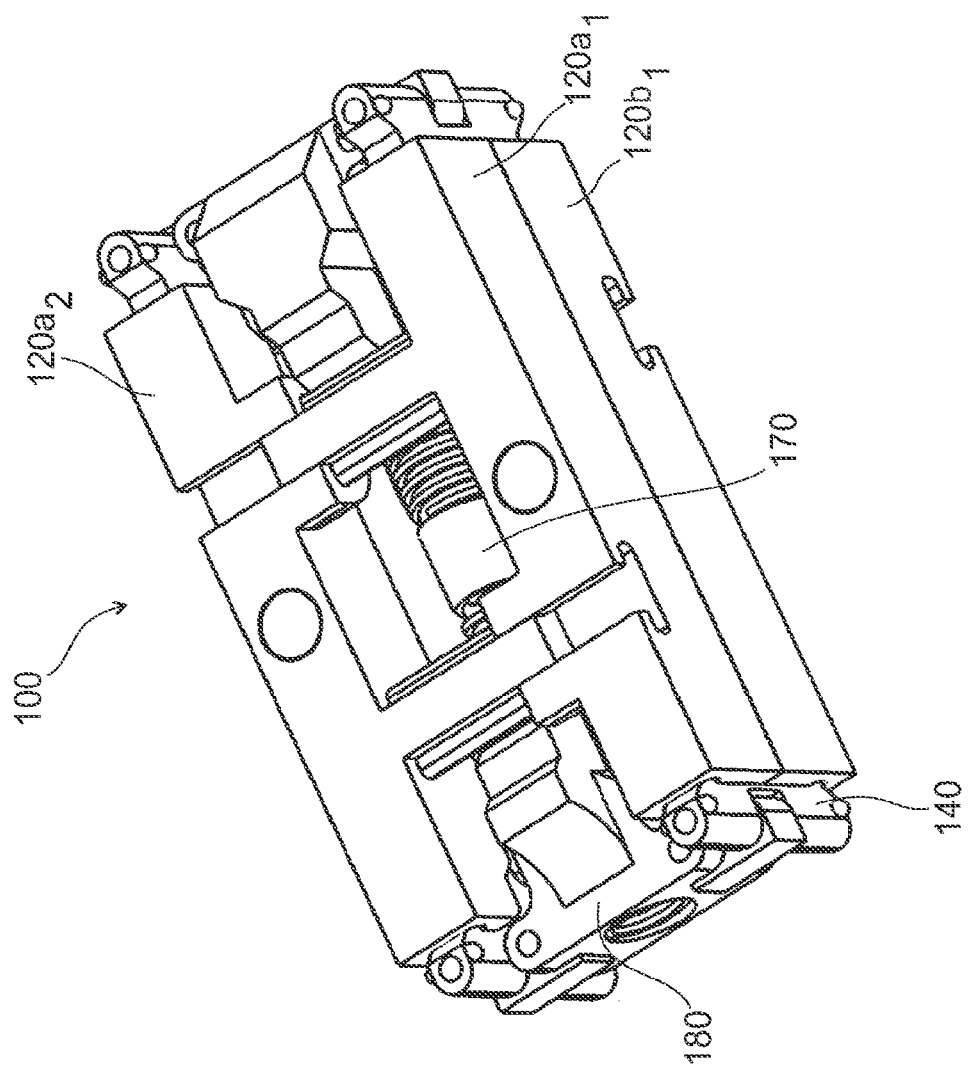

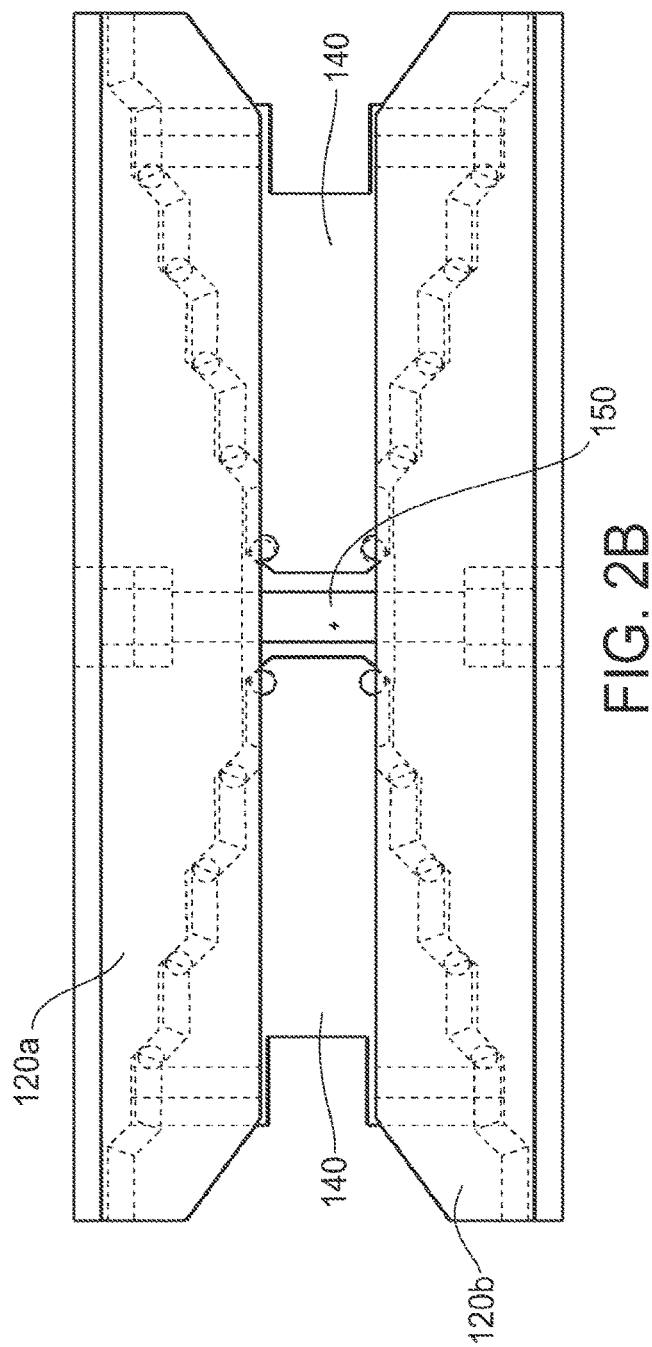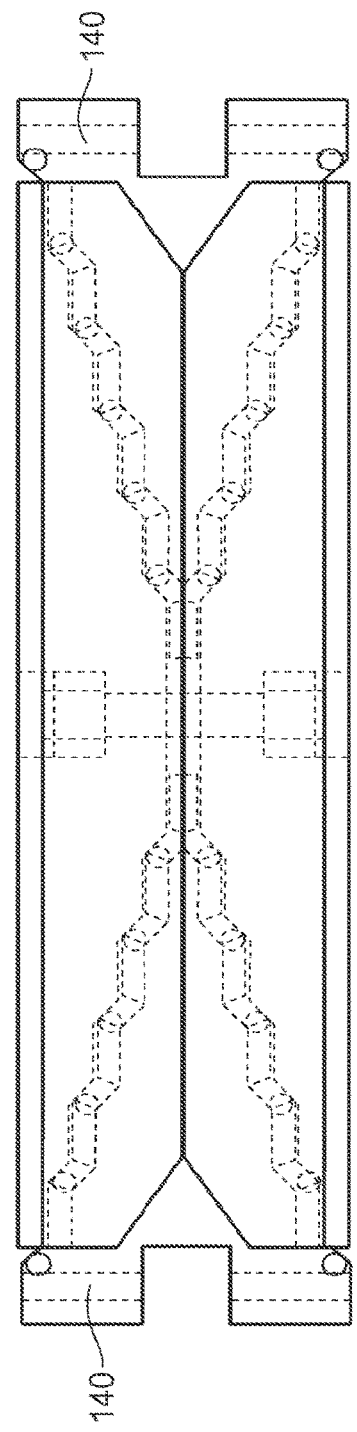

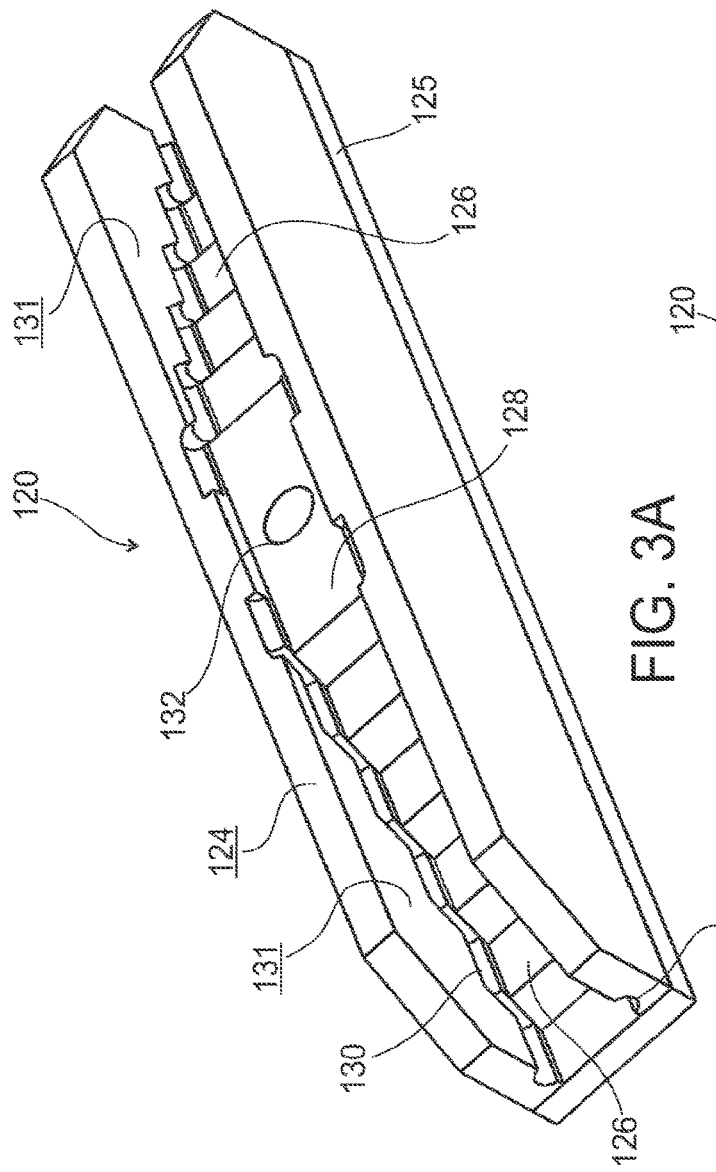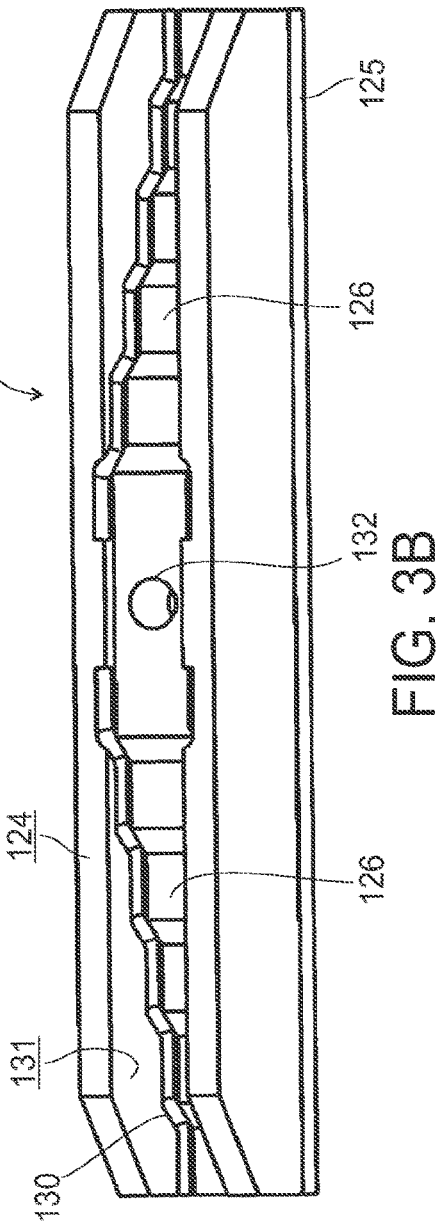

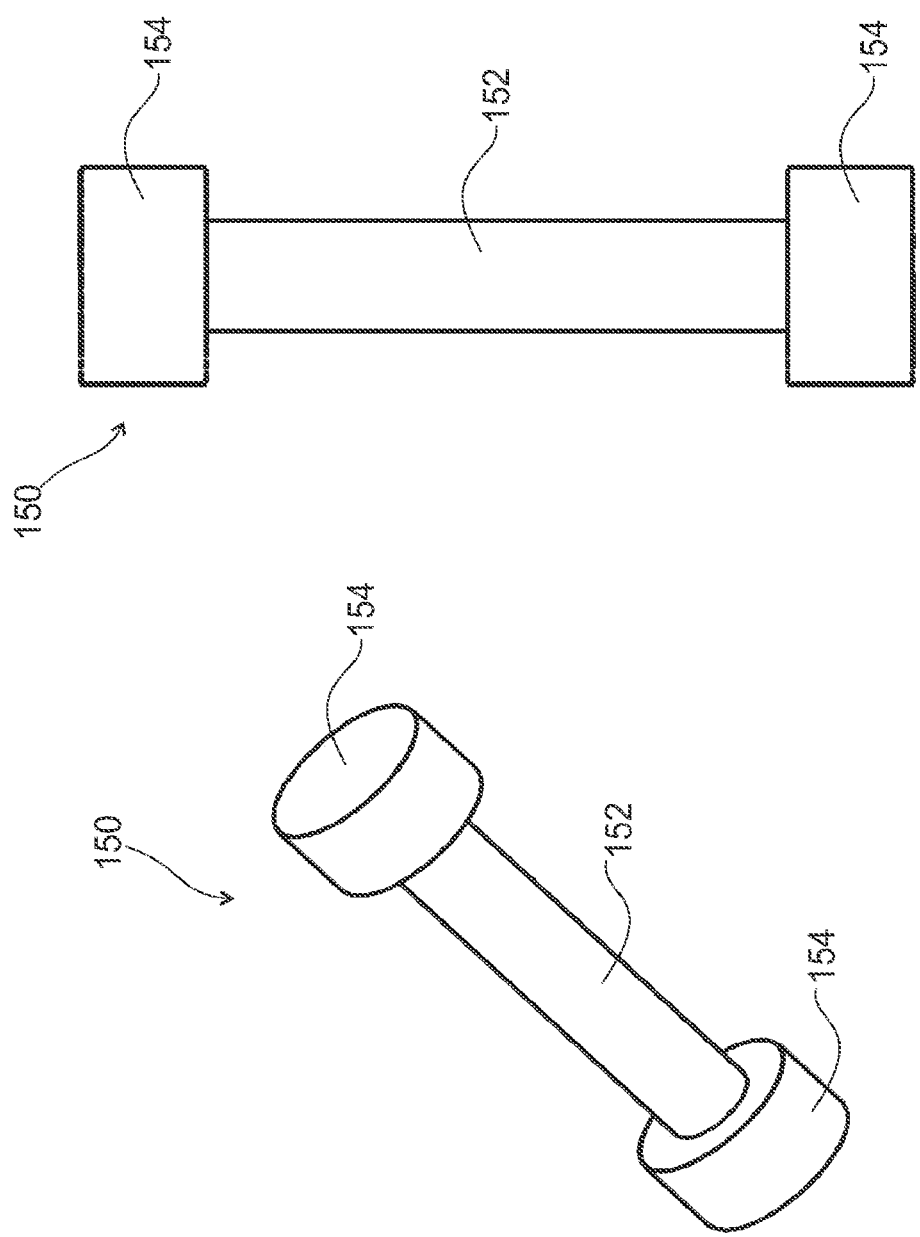

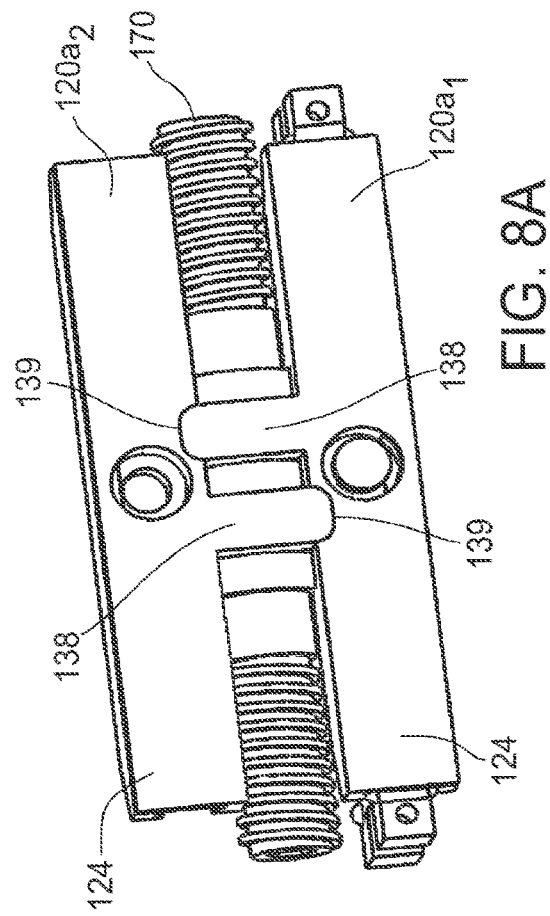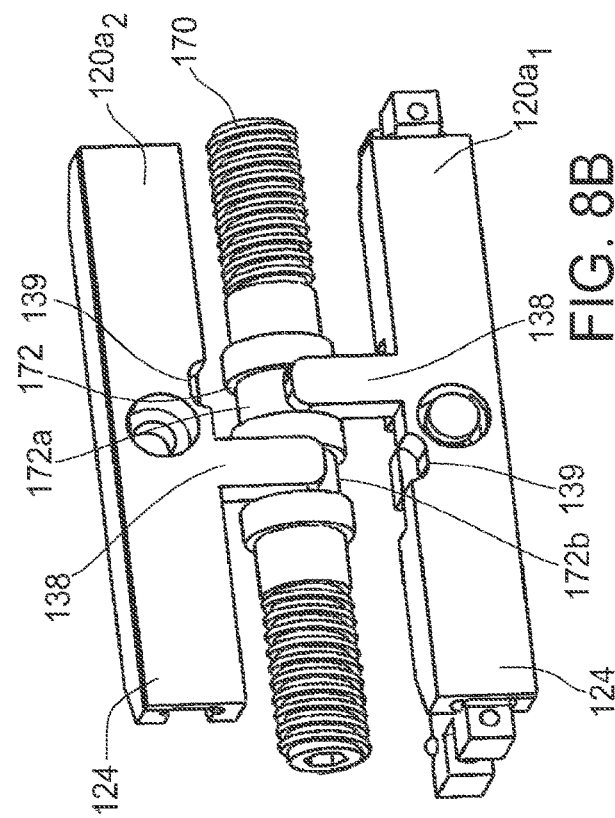

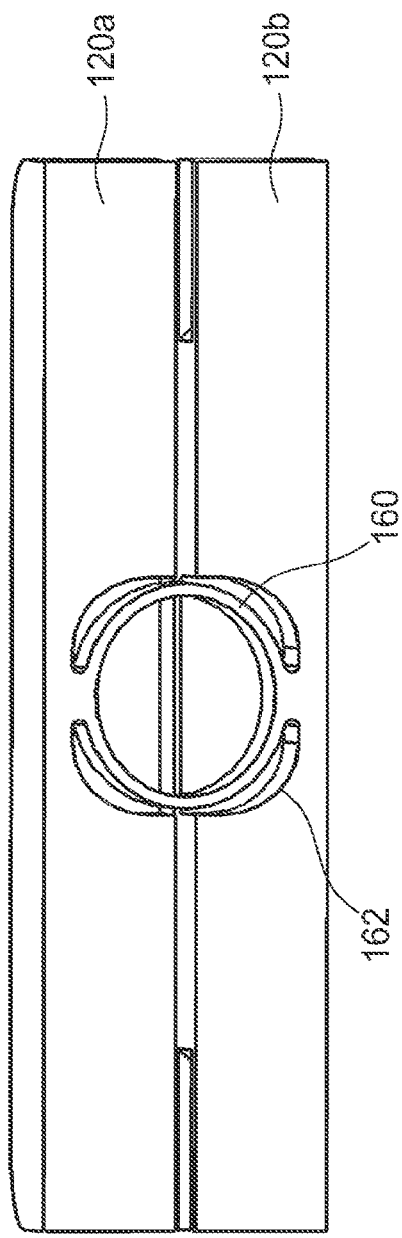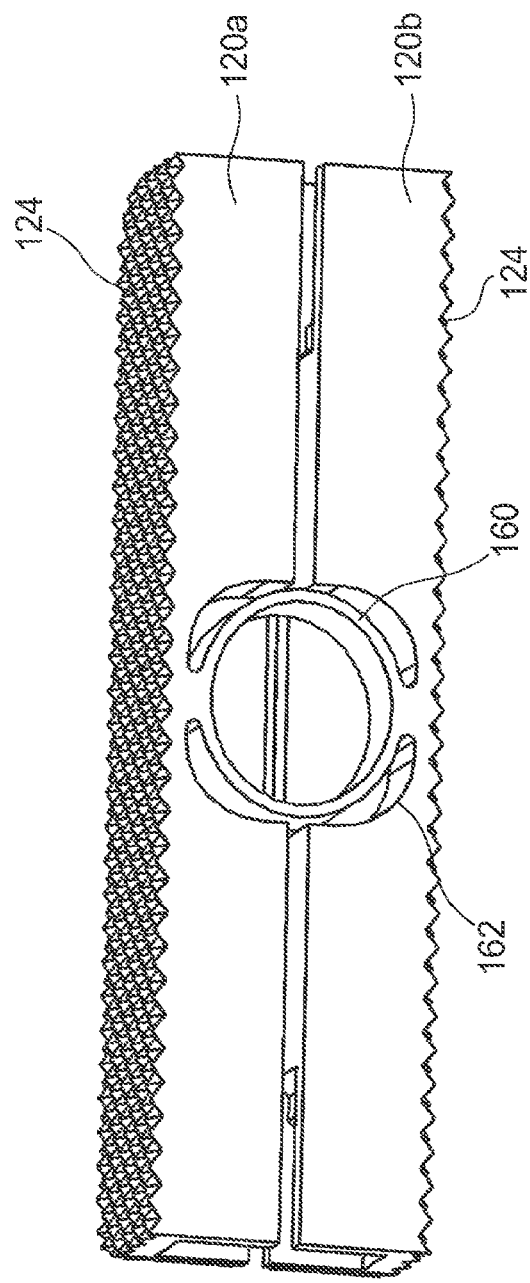

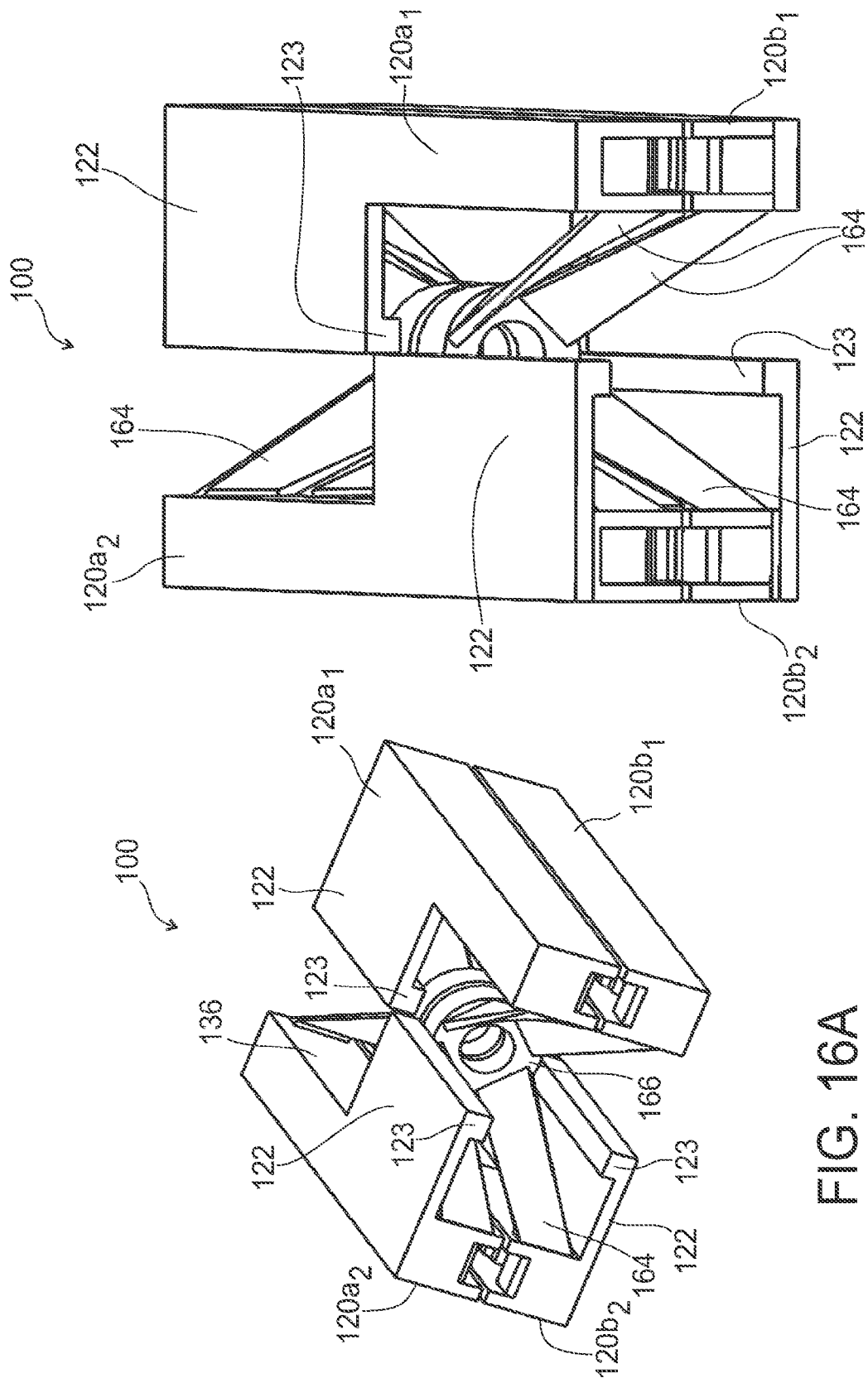

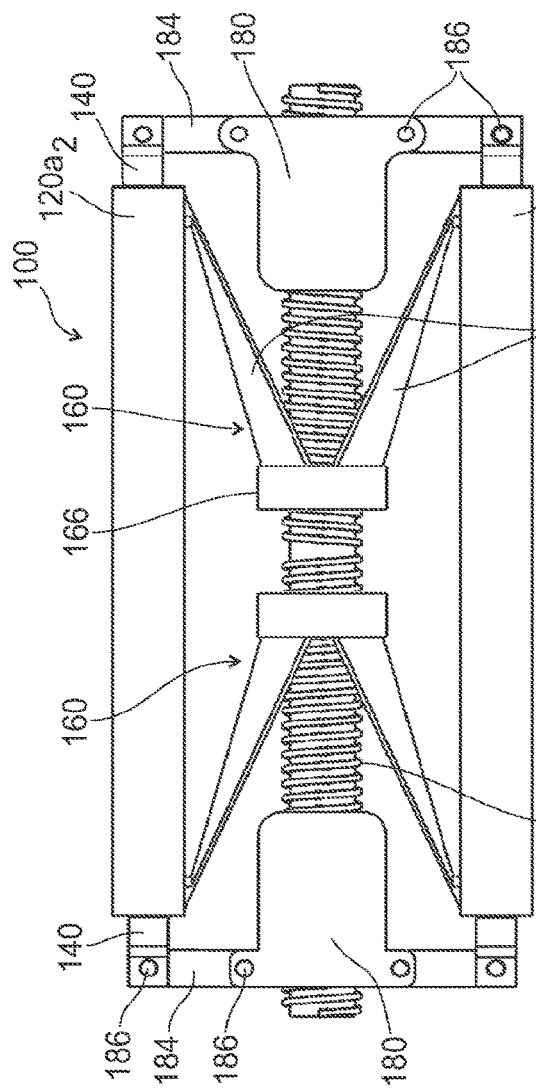
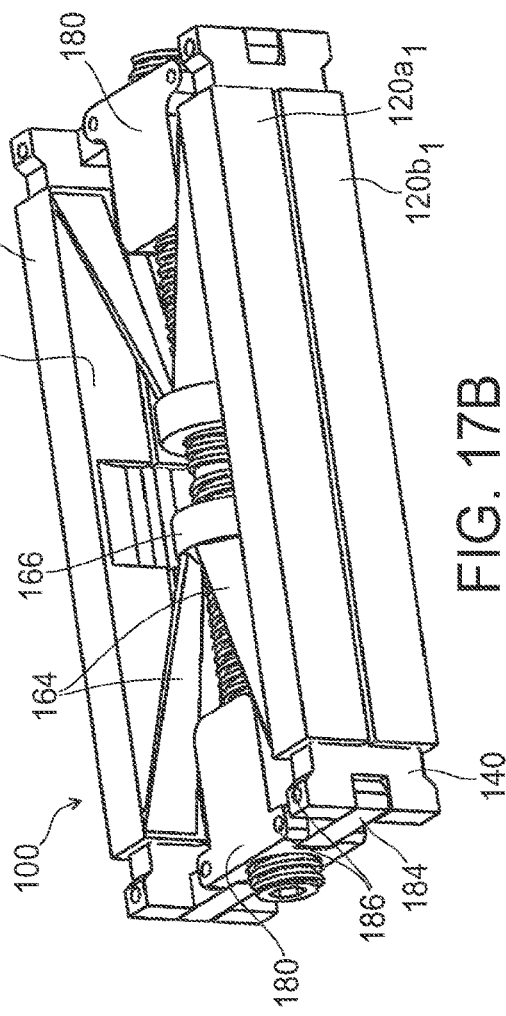
FIG. 17A
FIG. 17B

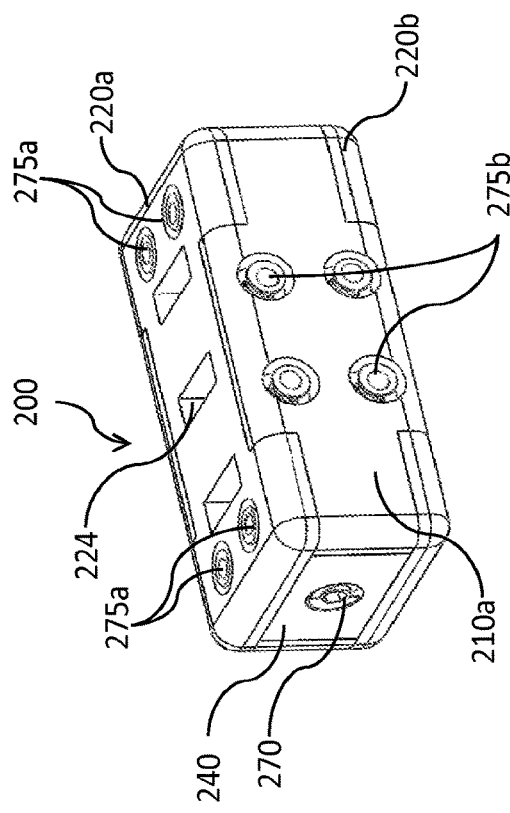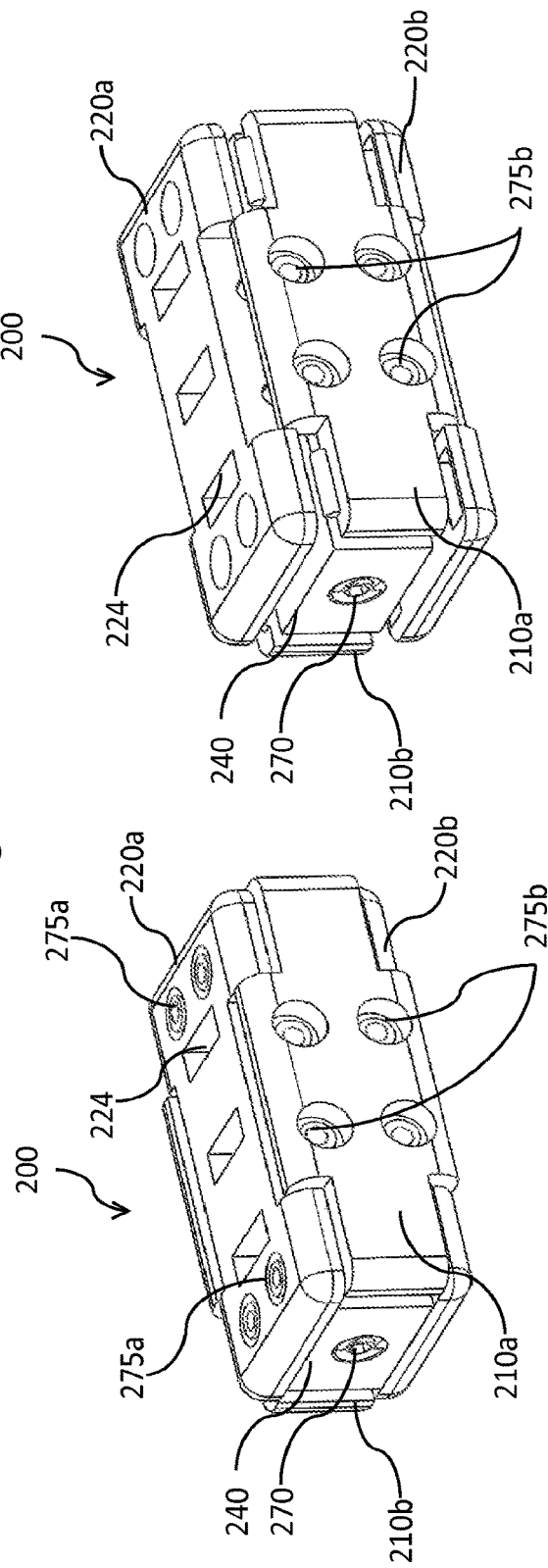

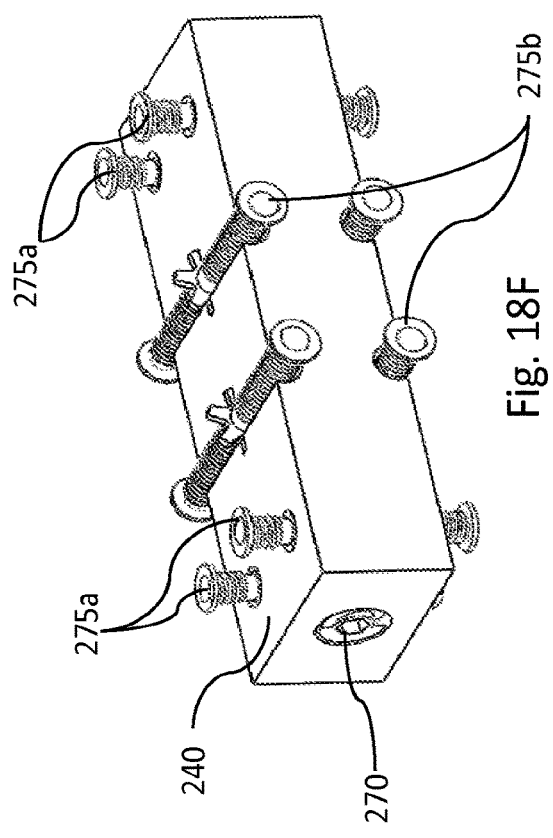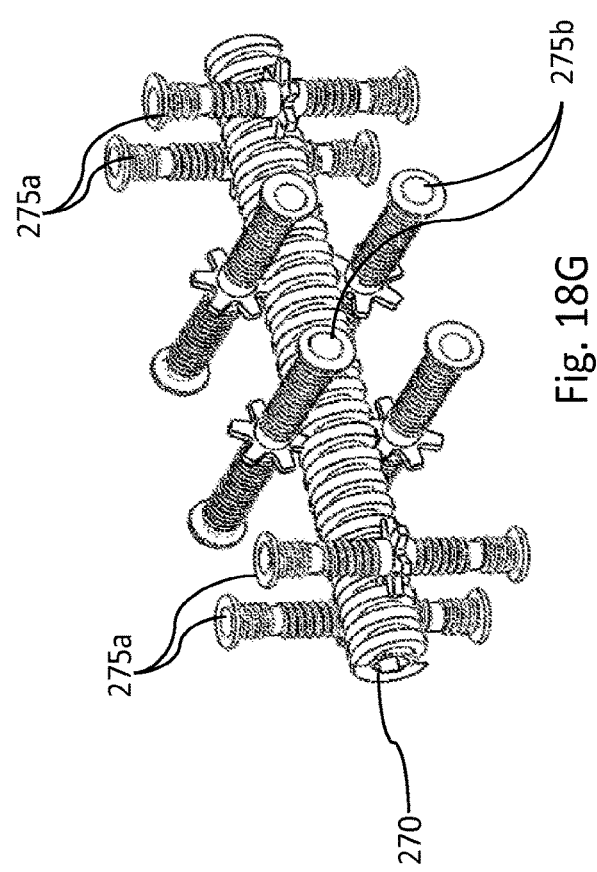

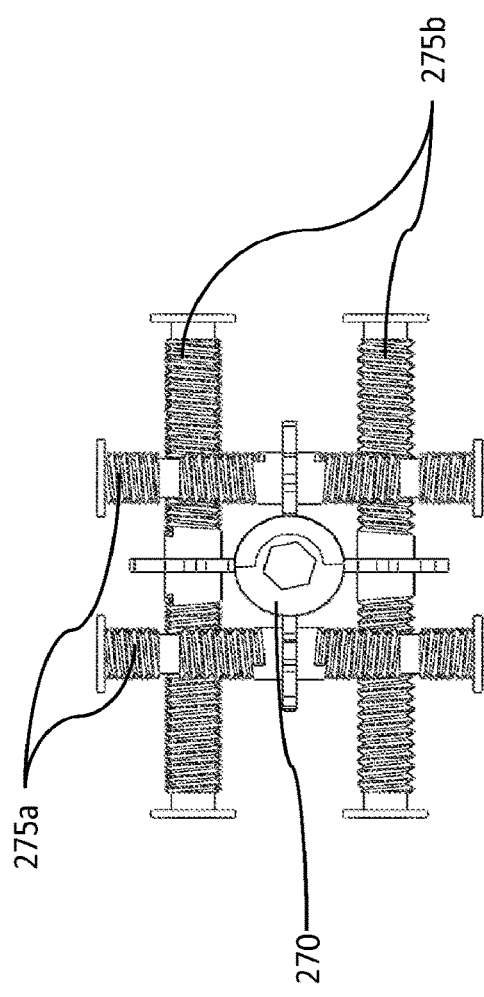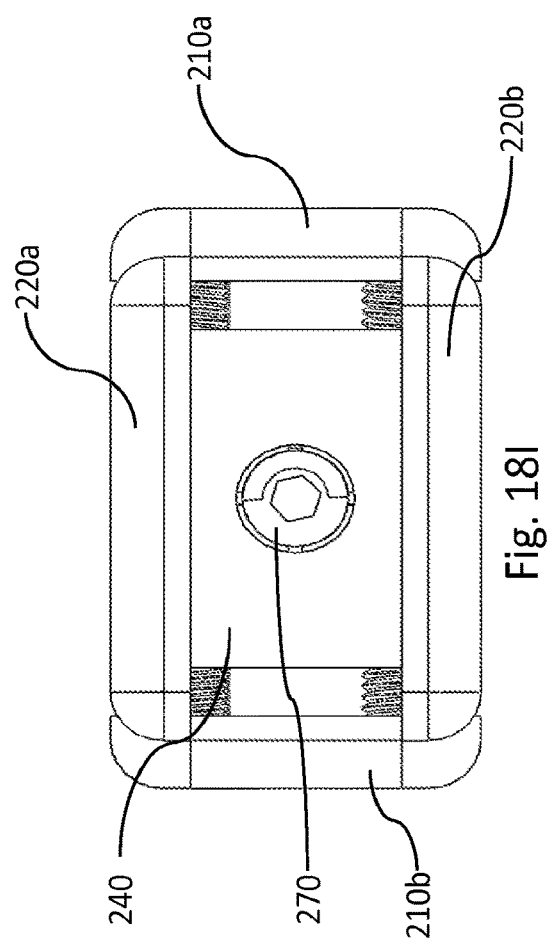
Fig. 18H
Fig. 18I

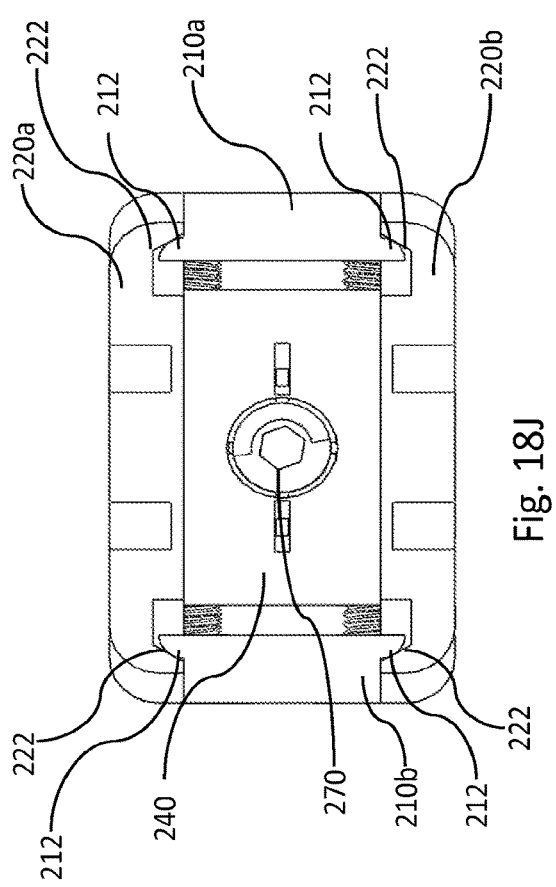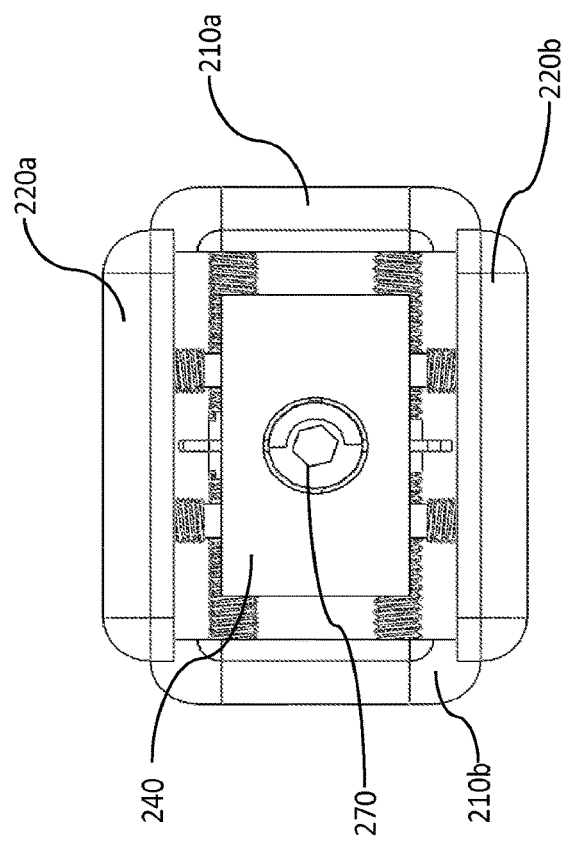

EXPANDABLE INTERVERTEBRAL CAGE

CROSS REFERENCE TO PRIORITY APPLICATION

This application is a continuation of U.S. application Ser. No. 15/500,969, filed Feb. 1, 2017, titled "Expandable Intervertebral Cage" (now U.S. patent Ser. No. 10/322,009), which claims the benefit of U.S. Provisional Application No. 62/031,955, filed Aug. 1, 2014, which are incorporated herein by reference in their entirety.

TECHNICAL FIELD

This disclosure relates to neurosurgical and orthopedic fixation systems.

BACKGROUND

Spinal interbody fusion is a frequently performed procedure to treat various disorders such as degenerated disk disease, spondylolisthesis, trauma, infection, tumor and deformity. Usually, surgery involves placement of screws into the vertebral body through the vertebral pedicle and/or placement of an interbody cage with bone grafts into the disc space. Types of spinal fusion depend on the approach type such as posterior, transforaminal, lateral, etc. Although these approaches claim to be minimally invasive, they still require open incisions for cage and screw placement as well as compression and/or distraction of vertebral bodies. Improvements in the devices' design enhance spinal fusion as well as minimize the invasiveness of the surgical implantation, which are desirable traits in clinical practice.

SUMMARY

Presented are systems and methods for providing fusion and distraction between adjacent vertebral bodies. An aspect of the present disclosure is directed to an intervertebral cage including an upper bar and an opposing lower bar. The cage can further include a separator movable between the upper bar and the lower bar to cause movement of the upper bar towards and away from the lower bar. The cage can also include a pin having a first end extending into an opening provided in the upper bar and a second end extending into an opening provided in the second bar.

Another aspect of the present disclosure is directed to an intervertebral cage including a first upper bar and opposing first lower bar. The cage can also include a first and second separator movable between the first upper bar and the first lower bar to cause movement of the first upper bar towards and away from the first lower bar. The cage can further include a second upper bar and opposing second lower bar and a third and fourth separator movable between the second upper bar and the second lower bar to cause movement of the second upper bar towards and away from the second lower bar. The cage can also include a threaded rod, where each of the bars include an arm extending from a side surface of each of the corresponding bars, the arms engaging the threaded rod.

The details of one or more implementations of the invention are set forth in the accompanying drawings and the description below. Other features, objects, and advantages of the invention will be apparent from the description and drawings, and from the claims.

DESCRIPTION OF DRAWINGS

The device is explained in even greater detail in the following exemplary drawings. The drawings are merely exemplary to illustrate the structure of preferred devices and certain features that may be used singularly or in combination with other features. The invention should not be limited to the implementations shown.

FIG. 1 is a perspective view if an example intervertebral cage;

FIG. 2B is a front view of the example bar pair of FIG. 2A in an expanded configuration;

FIG. 2C is a front view of the bar pair of FIG. 2A in an unexpanded configuration;

FIGS. 3A and 3B are perspective views of an example bar;

FIG. 5A is a perspective view of an example pin;

FIG. 5B is a front view of an example pin;

FIGS. 8A and 8B are top perspective views of opposing upper bars and threaded rod;

FIG. 11A is a front view of example bar pair connected with a compliant mechanism;

FIG. 11B is a perspective view of the example bar pair connected with a compliant mechanism of FIG. 11A;

FIGS. 16A and 16B are perspective views of an example intervertebral cage with overhanging supports and compliant mechanisms;

FIG. 17A is a top view of an example intervertebral cage with compliant mechanisms in a horizontally expanded configuration;

FIGS. 17B and 17C are perspective views of the example intervertebral cage with compliant mechanisms of FIG. 17A;

FIGS. 18A-18C are perspective views of an example intervertebral cage;

FIG. 18F is a perspective view of a central component and actuating members;

FIG. 18G is a perspective view of the actuating members;

FIG. 18H is an end view of the actuating members;

FIG. 18I is an end view of the example cage of FIG. 18A in horizontally expanded configuration;

FIG. 18J is a sectional view of the example cage of FIG. 18A in a horizontally expanded configuration; and FIG. 18K is an end view of the example cage of FIG. 18A in a vertically and horizontally expanded configuration.

DETAILED DESCRIPTION

Figure 2A:
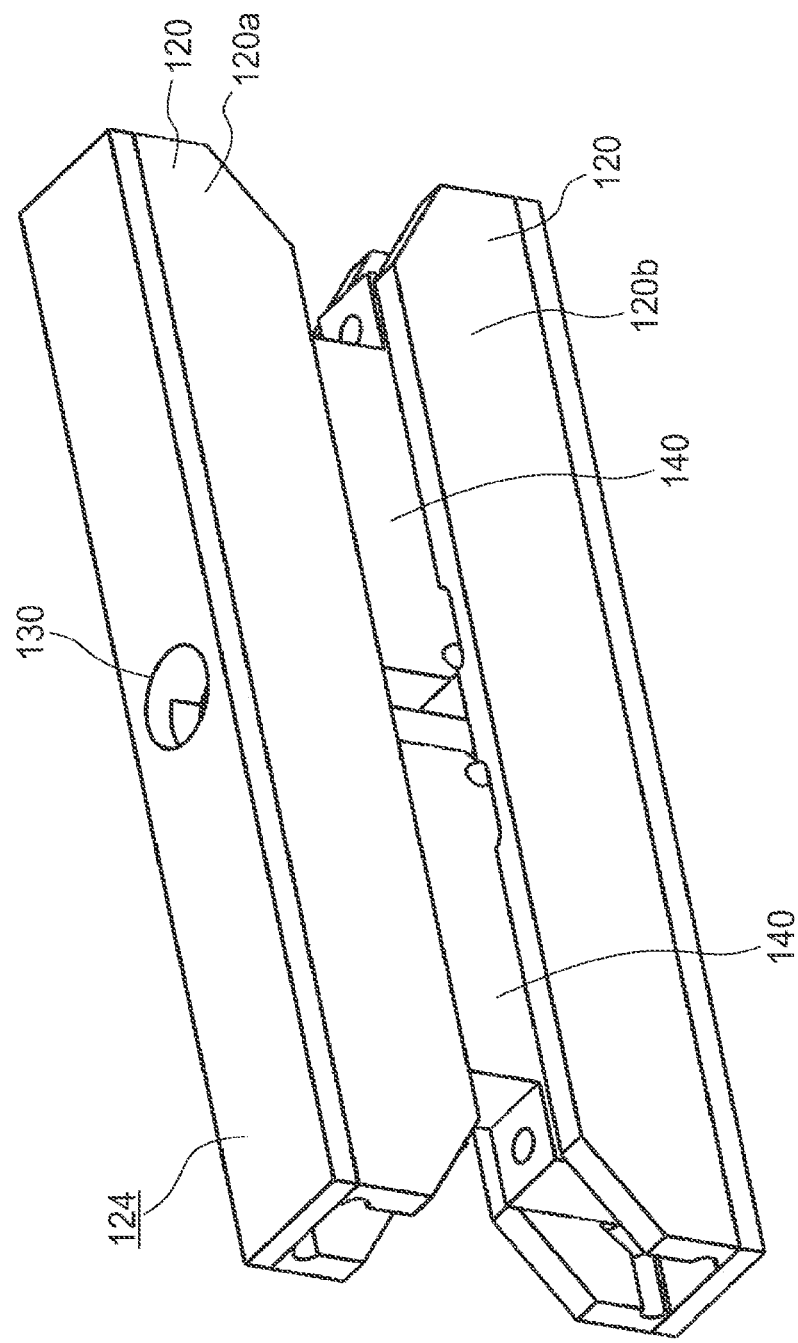
FIG. 2A is a perspective view of an example bar pair.

Certain exemplary implementations of an expandable intervertebral cage used to facilitate fusion between two vertebral bodies will now be described with reference to the drawings.

The cage 100 is designed for implantation and fusion between two vertebrae. The cage 100 can be implanted, for example between adjacent cervical, thoracic, lumbar, or sacral vertebrae. In non-expanded state, the cage 100 can be inserted through a small incision into the disc space or between two adjacent bones. Once expanded, the cage 100 can be used to provide distraction between the adjacent vertebrae or bones. As will be described in more detail below, the cage 100 can expand horizontally and/or vertically. For example, once positioned as desired by a medical professional, the cage 100 can be expanded in a horizontal direction; for example, in the horizontal plane of the intervertebral space in which the cage 100 is located. The cage 100 can also be expanded in a vertical direction to increase the vertical separation between the adjacent vertebrae. The horizontal expansion can be performed before the vertical expansion. A single actuator, or plurality of actuating devices, can be used to provide horizontal and vertical expansion. In one example, an actuator(s) can be used to first cause horizontal expansion followed by vertical expansion. In this way, a low height and width profile of the unexpanded cage 100 can be used for implantation and then with use of an actuator, the width and height profile can be expanded as desired. The space between the deployed components of the cage 100 can be accessed for placement of a bone filling material.

FIG. 1 is a perspective view of an example intervertebral cage 100. The cage 100 can include two pairs of upper and opposing lower longitudinal bars 120, e.g., upper and lower bars $120a_1$, $120b_1$ and upper and lower bars $120a_2$, $120b_2$. Each pair includes an upper bar 120a and a lower bar 120b and the pairs are spaced from one another across the vertical midline of the cage 100. As will be described in more detail below, the lateral and vertical space between the bars 120 can be increased/decreased and the cage 100 is expanded/retracted (the cage 100 illustrated in FIG. 1 is expanded in only the lateral direction). A separator 140 can be used to provide define a distance/separation between the upper and lower bar pairs 120a, 120b and the height of the cage 100 in an expanded configuration. As will be described below, a threaded rod 170 and spacer 180 can be used to control/limit lateral and vertical expansion between adjacent bar pairs $120a_1$, $120b_1$ and $120a_2$, $120b_2$.

FIG. 2A is a perspective view of an example bar pair including upper bar 120a and lower bar 120b. FIG. 2B is a front view of the example bar pair 120a, 120b of FIG. 1 in an expanded configuration. FIG. 2C is a front view of the example bar pair 120a, 120b of FIG. 1 in an unexpanded configuration. As illustrated in FIGS. 2B and 2C, and as will be described in more detail below, the separator 140 can be movable between the upper bar 120a and the lower bar 120b to cause movement of the bars towards and away from each other.

Figure 7:
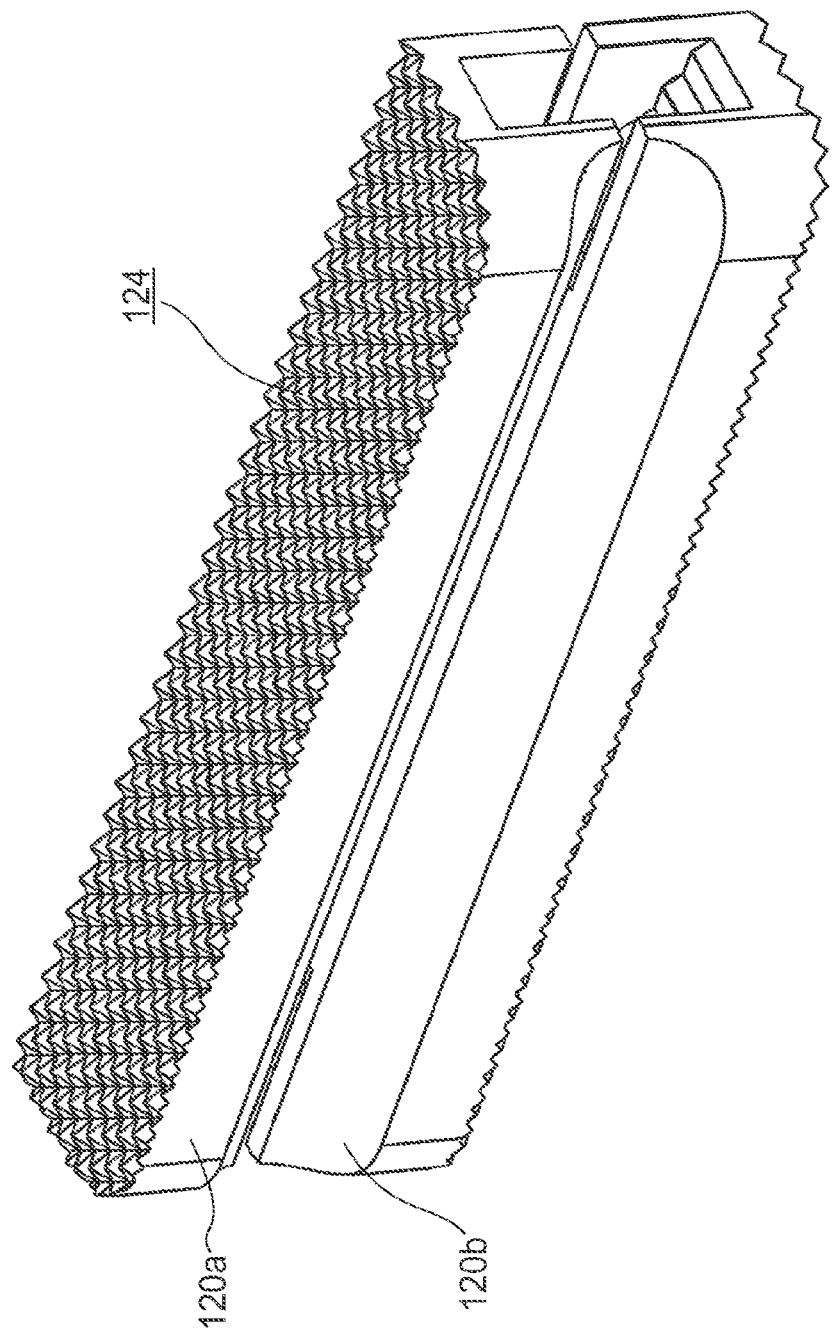
FIG. 7 is a perspective view of example upper and lower bar pair.

FIGS. 3A and 3B are perspective views of an example upper bar 120a and/or lower bar 120b. The bar can include a top surface 124 and an opposing vertebral body contacting surface 125 for contacting the vertebral endplates of the adjacent vertebral bodies. The vertebral body contacting surface 125 can bend, deform or consist of specific surface area (either of irregular or regular shape) to accommodate the endplate of the adjacent vertebral body. The vertebral body contacting surface 125 can also consist of a sloping surface to intentionally induce uneven expansion. Likewise, the vertebral body contacting surface 125 of the upper and lower bars 120a, 120b can include teeth or ridges for engaging the endplates of the adjacent vertebral bodies as shown, for example, in FIG. 7. The teeth can provide engagement and/or increased purchased between the cage 100 and the adjacent vertebral bodies. The teeth can have a pyramid shape (polygonal base and triangular faces that meet at a common point) or any other shape that can be used to provide increased friction, surface area contact and engagement between the bar 120 and the adjacent vertebral endplate. It is also contemplated that the vertebral body contacting surface 125 can include any type of biological or non-biological coating to enhance bone growth and attachment (fusion) with the cage 100.

As illustrated in FIGS. 3A and 3B, the bar 120 can also include a contact surface 126 for contacting a corresponding surface 142 provided on the separator 140 such that movement of the separator 140 along the bar's contact surface 126 can increase and/or decrease the spacing between the upper and lower bars 120a, 120b. Initially a lateral bar pair can be provided in the unexpanded configuration as illustrated in FIG. 2C. In the unexpanded configuration the separator 140 is provided on the contact surface 126 proximate the end of the bar 120. Movement of the separator 140 towards the midline of the bar 120 increases the spacing between the upper and lower bars 120a, 120b and drives the cage 100 from an unexpanded to a vertically expanded configuration.

As illustrated in FIGS. 3A and 3B, the contact surface 126 can be inclined towards the midline of the bar 120 and configured to engage a corresponding inclined contact surface 142 of the separator 140. As illustrated in FIGS. 2B-2C and 3A-3C, contact surface 126 can include an inclined stepped surface. Likewise, the contact surface 142 of the separator 140 can include a corresponding inclined stepped surface. Because the upper and lower bars 120a and 120b are under compression when implanted, the flats of the stepped contact surface 126 prevent the separator 140 from backing out when under pressure. Likewise, the distance between adjacent flats can define the discrete expansion value for each step (e.g., 1 mm, 2 mm, 3 mm, 4 mm). It is contemplated that the contact surface 126 and/or the corresponding contact surface 142 can define a straight/flat surface, a curved surface (e.g., convex, concave, etc.) or any other regular or irregular shaped surface. While the distance between flats of a stepped design can define the expansion value of the separator 140, an inclined design can have continuous expansion values ranging between, for example, 1 mm-4 mm.

Figure 3D:
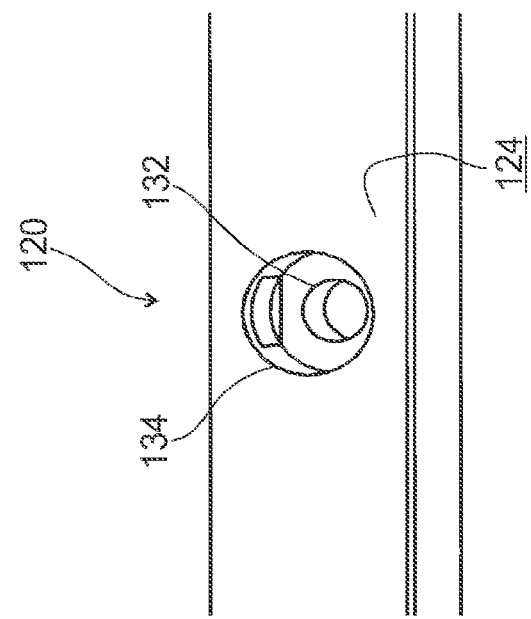
FIG. 3D is a partial top perspective view of an example bar.
Figure 3C:
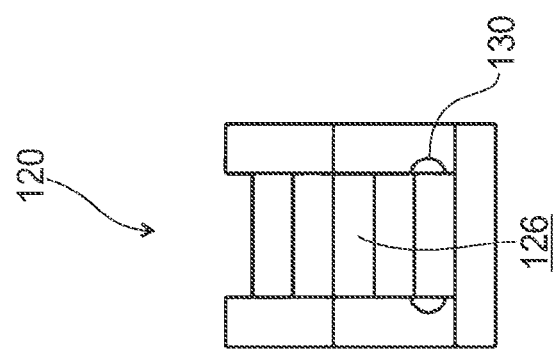
FIG. 3C is an end view of an example bar.

Though not illustrated, the upper and/or lower bars 120a, 120b can include a single contact surface 126. In another example, and as illustrated in FIGS. 3A and 3B, the bar 120 can include two contact surfaces 126 provided at opposite ends of the bar 120. The contact surfaces 126 can terminate at a stop surface 128 proximate the top surface 124 of the bar 120. In another example (not shown), the contact surfaces 142 can terminate at a common edge or intersection point, e.g., the intersection point of two separator contact surfaces provided on the bar 120. As provided in FIGS. 3A-3C, the bar 120 can include a groove 130 included on an inside surface 131 of the bar 120. The groove 130 can be inclined towards the midline of the bar 120 and configured to engage a corresponding projection 144 extending from a side surface 146 of the separator 140, illustrated in FIGS. 4A-4D. As illustrated in FIGS. 3A-3C, the groove 130 can be stepped and be provided proximate the contact surface 126. In another example (not shown), the groove 130 can be provided at any location on an inside surface 131 of the bar 120 separate from the location of the contact surface 126. In a further example (not shown), bar 120 does not include a contact surface 126 and the groove 130 can be provided on an inside surface 131 of the bar 120.

Figure 4B:
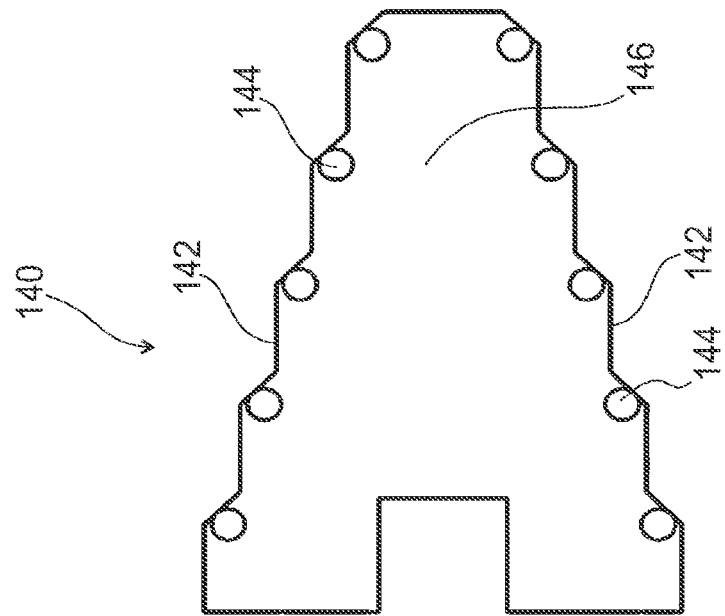
FIG. 4B is a side view of an example separator.
Figure 4A:
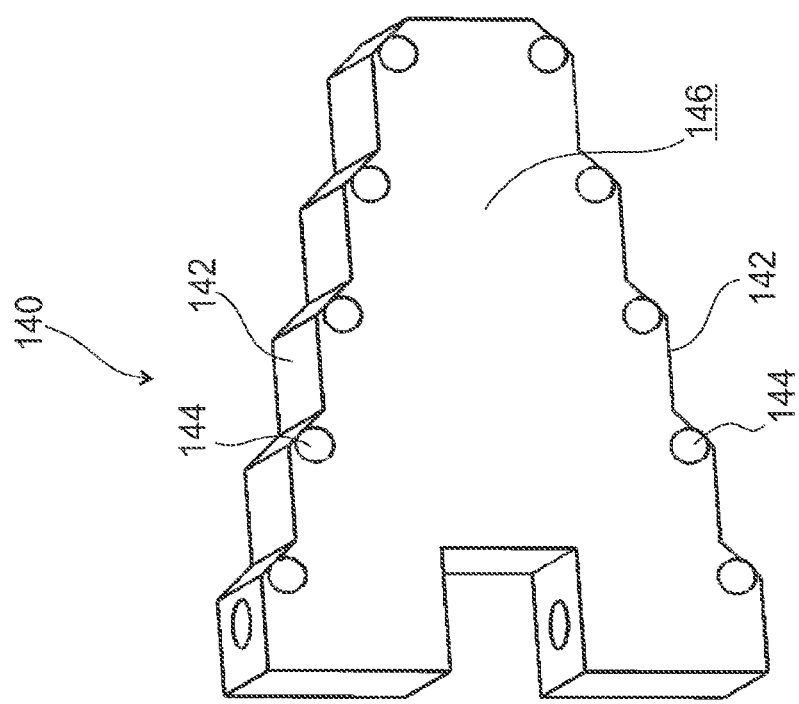
FIG. 4A is a perspective view of an example separator.
Figure 4D:
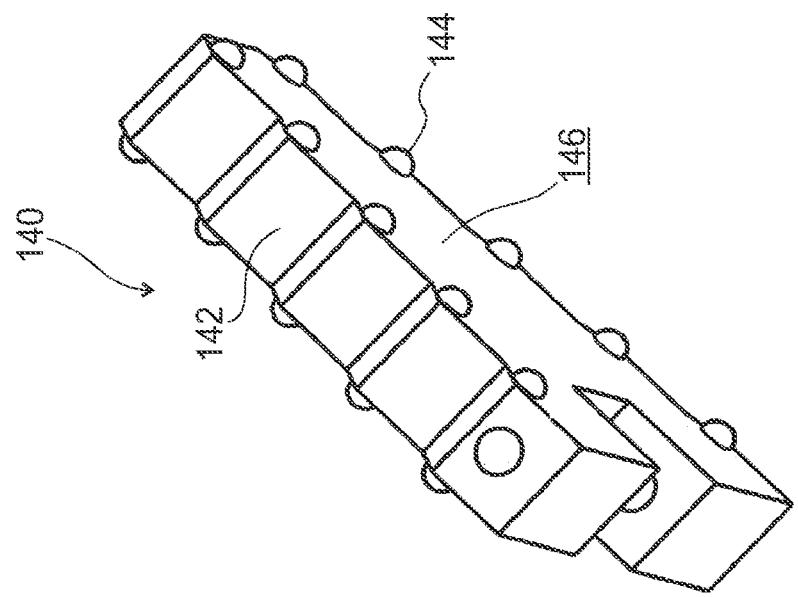
FIGS. 4C and 4D are perspective view of an example separator.
Figure 4C:
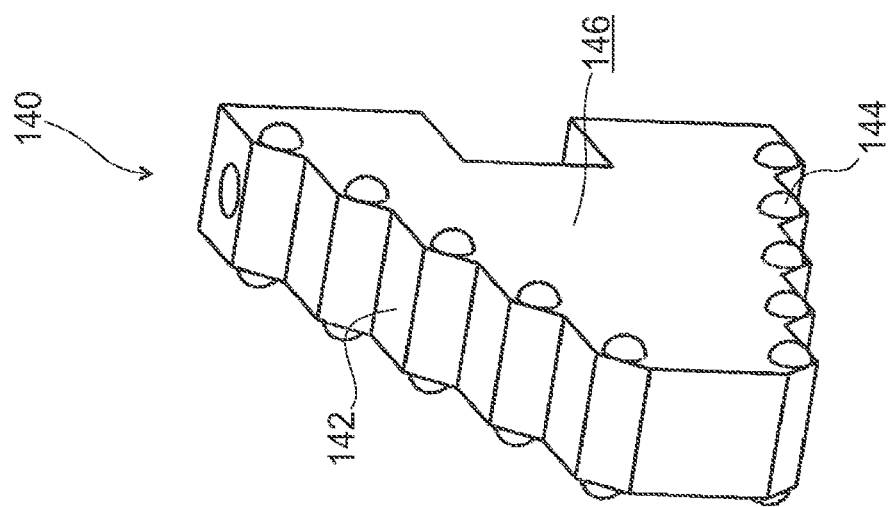
Figure 5D:
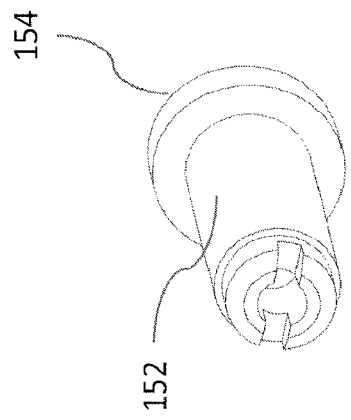
FIGS. 5C and 5D are perspective views of an example partial pin.
Figure 5E:
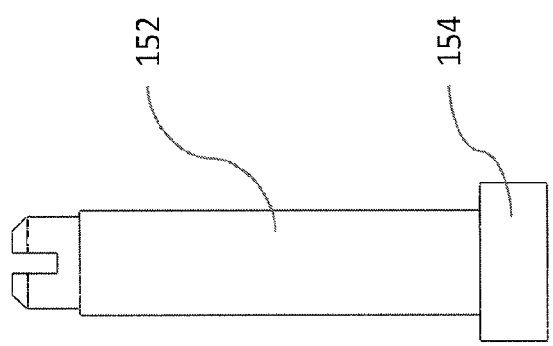
FIG. 5E is a front view of an example partial pin.
Figure 5C:
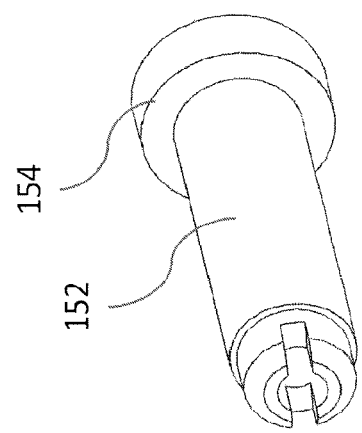
Figure 5G:
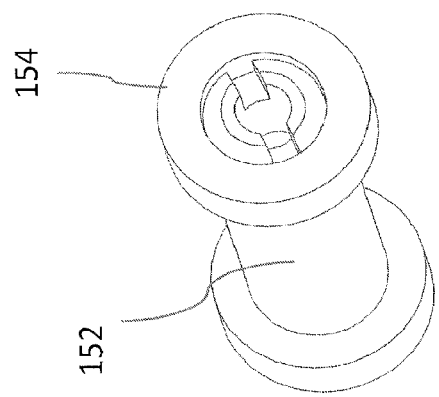
FIGS. 5F and 5G are perspective views of an example pin.
Figure 5F:
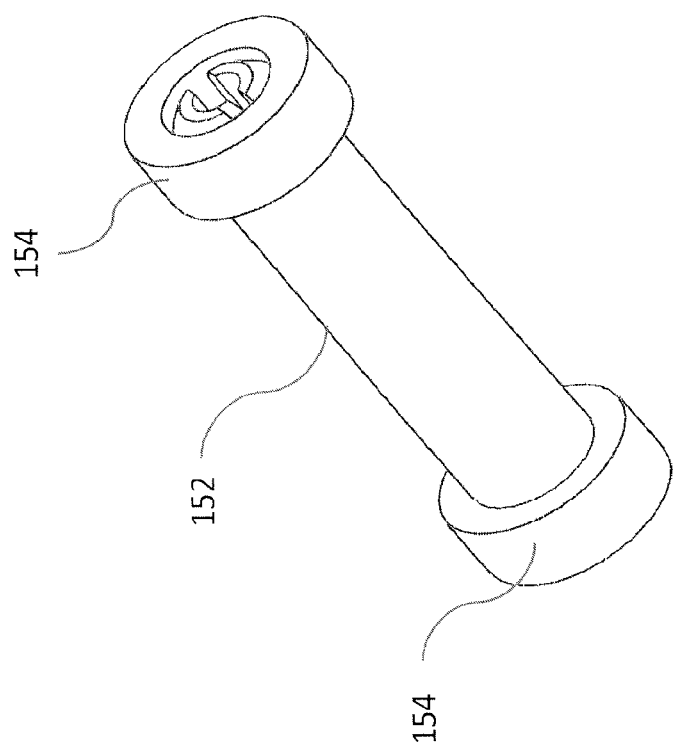

FIGS. 4A, 4C and 4D provide perspective views of an example separator 140. FIG. 4B is a side view of the example separator 140. As illustrated, the separator 140 can include an inclined and/or stepped contact surface 142. The projection 144 for engaging the groove 130 provided in the bar 120 can be located on the side of the separator 140 proximate the contact surface 142. The separator 140 can include a single projection 144 or a plurality of projections 144. The projections 144 can sized and shaped to slidably engage the groove 130. For example, the projection 144 can define a round/hemispherical shape, or any other regular or irregular shape that permits movement between the projection 144 and the groove 130. During use, engagement of the projection 144 and the groove 130 guides movement of the separator 140 with respect to the bar 120 from an unexpanded to expanded configuration, and vice versa. Engagement between the projection 144 and the groove 130 also helps to maintain contact and/or spacing between the contact surface 126 and the contact surface 142. FIGS. 5A and 5B provide a perspective and front view of an example pin 150. The pin 150 can include a main body 152 and a head 154. The main body 152 can include an elongated shaft extending between two head portions 154 where the heads 154 have a width/diameter greater than a width/diameter of the main body 152. The head 154 can be of a regular or an irregular shape and the pin 150 can consist of a symmetrical, as illustrated in FIG. 5A, or asymmetrical shape (not illustrated). The pin 150 extends through/into and is movable within an opening 132 in the bars 120. The pin 150 can be used to maintain alignment of the upper bar 120a and lower bar 120b during compression and distraction of the cage 100, i.e., movement between the unexpanded and expanded configuration. For example, the pin 150 can maintain the upper bar 120a and the lower bar 120b in a parallel configuration. The upper bar 120a and/or lower bar 120b can include a recessed opening 134 as illustrated in FIG. 3D showing a partial top perspective view of the top surface 124 of an example bar 120. The recessed opening 134 can have a width/diameter larger than the width/diameter of the main opening 132 and can be sized and configured to receive the head 154 of the pin 150. The depth of the recessed opening 134 can define the limits of expansion of the cage 100. That is, as the bottom of the heads 154 of the pin 150 impact/contact the bottom surface of the recessed opening 134 the cage 100 is prevented from further expansion. Accordingly, the distance between the heads 154 of the pin 150 can define the amount of expansion between the upper bar 120a and the lower bar 120b. Movement of the pin 150 within the openings 132 provided in the upper and lower bars 120a, 120b also prevents the bars 120 from shearing, that is, the pin 150 prevents the bars 120 moving from left to right with respect to each other. The pin 150, including the main body 152 and head(s) 154 can have unitary construction. In another example, illustrated in FIGS. 5C-5G, the main body 152 and head(s) 154 can be constructed from separate pieces coupled during assembly of the cage 100. For example, the main body 152 can be inserted through/into the main opening 132 of the upper and lower bars 120a, 120b and the heads 154 can be coupled (permanently and/or removably coupled) to the opposing ends of the main body 152. The main body 152 and head 154 can be coupled via press fit, snap fit, or any other form of mechanical fastening.

Figure 6A:
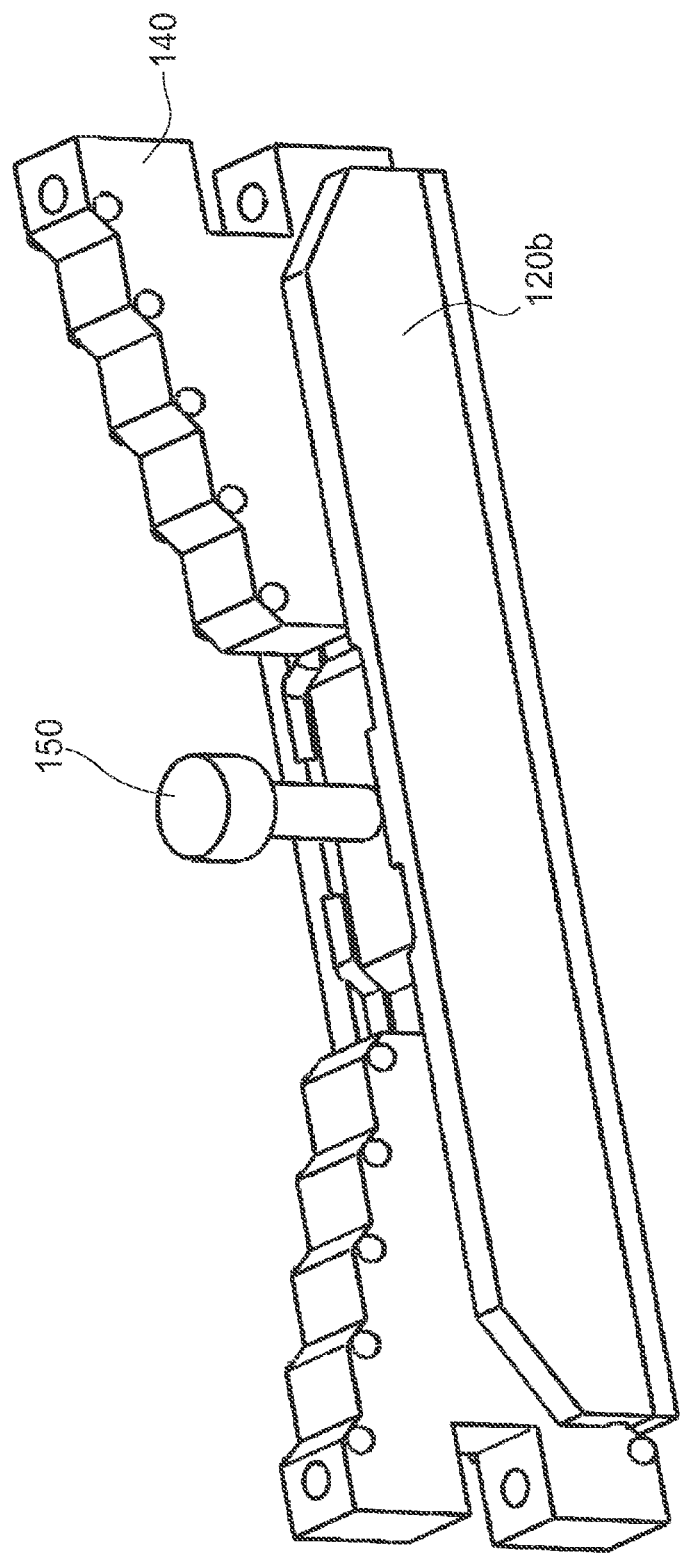
FIG. 6A is a perspective view of an example lower bar, separators, and pin.
Figure 6B:
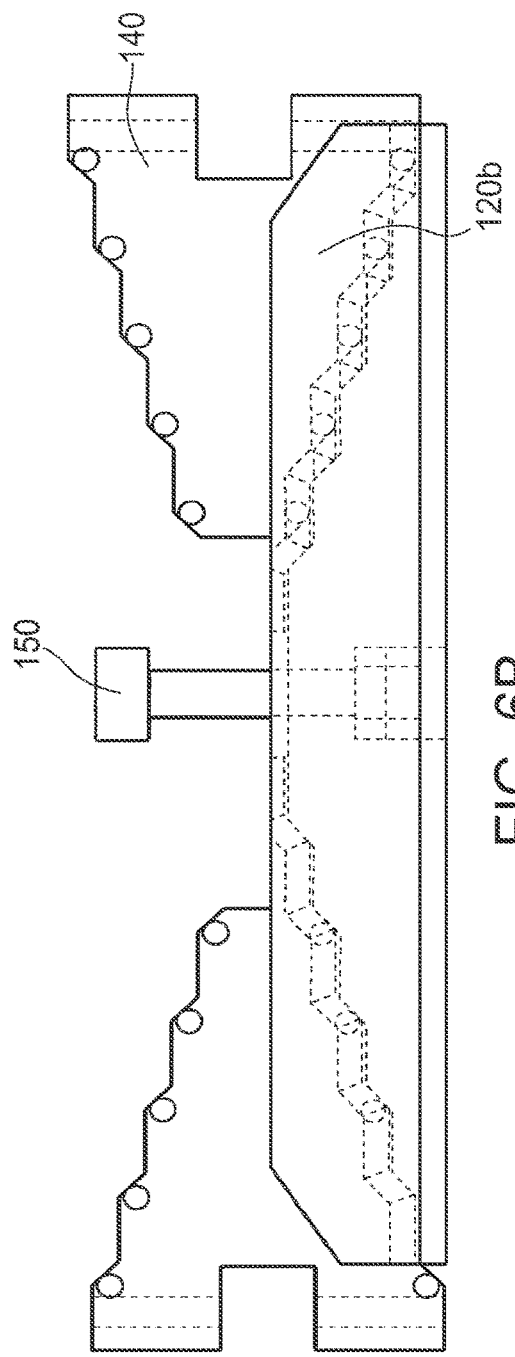
FIG. 6B is a front view of an example lower bar, separators, and pin in an unexpanded configuration.
Figure 6C:
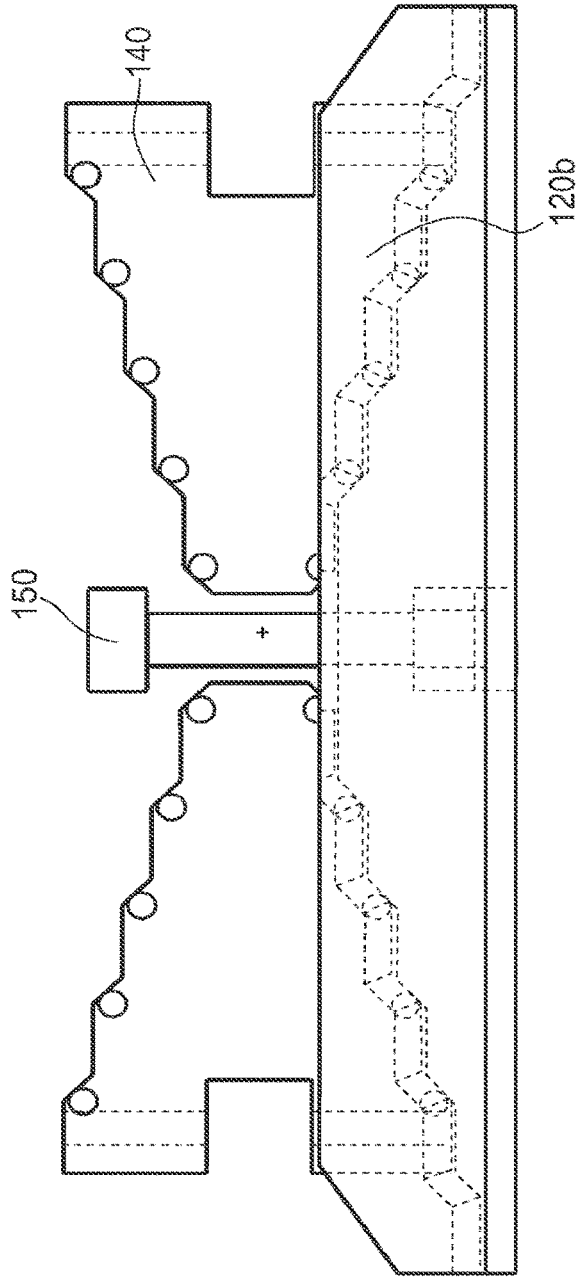
FIG. 6C is a front view of an example lower bar, separators, and pin in an expanded configuration.

FIGS. 6A-6C show an example front view of an assembled lower bar 120b, separator 140 and pin 150. FIGS. 6A and 6B illustrate the lower bar 120b and separators 140 in an unexpanded configuration and FIG. 6C illustrates the lower bars 120b and separators 140 in an expanded configuration.

Figure 8C:
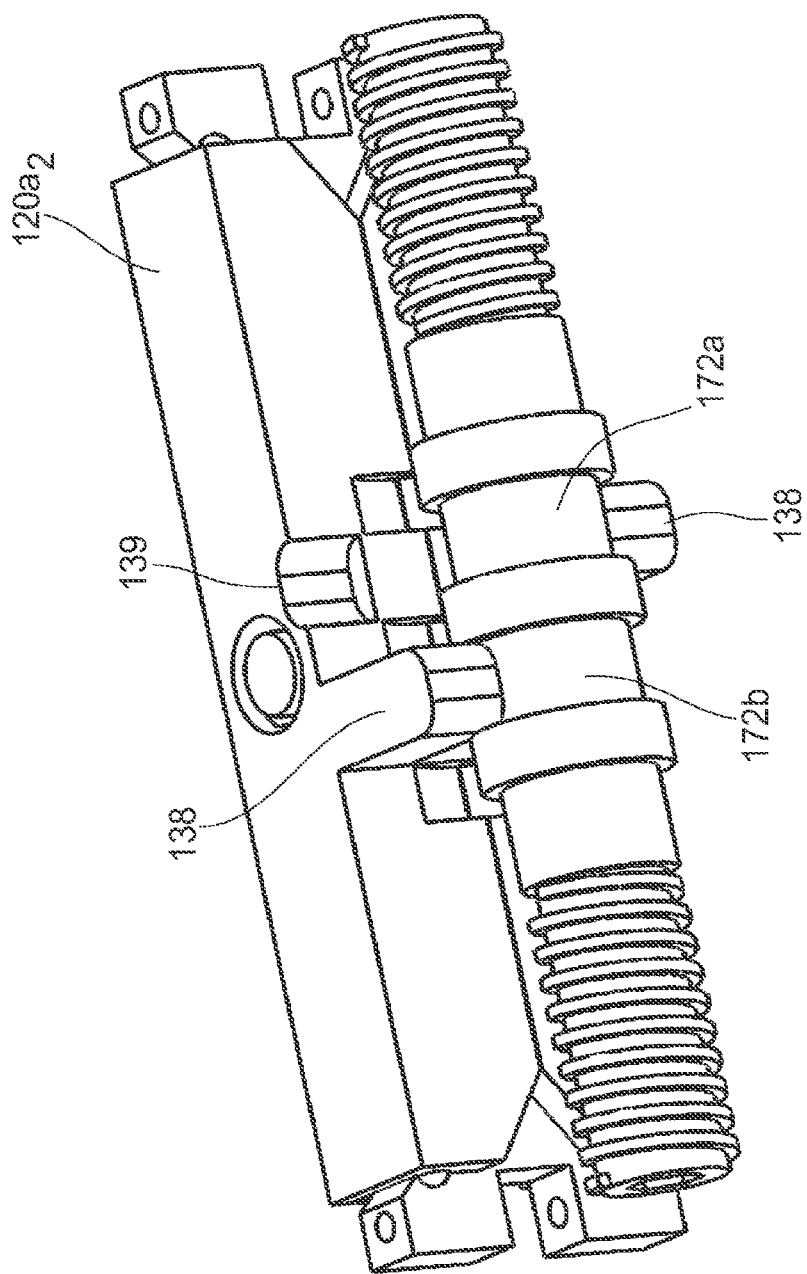
FIG. 8C is a perspective view of an example threaded rod and upper and lower bar pair.

As outlined above, a threaded rod 170 can be used for controlling/limiting lateral and vertical expansion between adjacent bar pairs $120a_1$, $120b_1$ and $120a_2$, $120b_2$. FIGS. 8A and 8B illustrate a top perspective view of example threaded rod 170 opposing upper bars $120a_1$ and $120b_1$. FIG. 8C is a perspective view of the example threaded rod 170 and upper and lower bar pair $120a_2$ and $120b_2$. While the example cage 100 includes two upper and a lower bar pairs $120a_1$, $120b_1$ and $120a_2$, $120b_2$, it is contemplated that cage 100 can also include a single pair of upper and lower bars 120a, 120b used in conjunction with a single actuator, or plurality of actuating devices, to provide horizontal and/or vertical expansion. For example, FIG. 8C illustrates an example of a cage 100 including a single pair of upper and lower bars 120a, 120b used in conjunction with a threaded rod.

FIGS. 8A and 8B show a top view of upper bars $120a_1$ and $120a_2$ in an unexpanded (FIG. 8A) and horizontally expanded (FIG. 8B) configuration. The space between opposing upper bars $120a_1$, $120a_2$ can be widened when the cage is expanded in the horizontal/lateral direction. Likewise, the space between opposing lower bars $120b_1$ and $120b_2$ can be widened when the cage is expanded in the horizontal/lateral direction. As provided in FIGS. 8A-8C, at least one of the bars 120 includes an arm 138 extending from a top surface 124 of the bar 120. For example, as illustrated in FIGS. 8A-8C, each bar 120 of the upper and lower bar pairs $120a_1$, $120b_1$ and $120a_2$, $120b_2$ include an arm 138 extending from a top surface 124 of the bar 120. The arm 138 extends in a direction towards the adjacent bar pair and engages the threaded rod 170. The threaded rod 170 can include a channel(s) 172 for engaging the arms 138 such that the arms 138 are movable (in a perpendicular direction) with respect to the threaded rod 170. For example, as the threaded rod 170 rotates, the arm 138 is maintained within the channel 172 and the shear movement between the opposing bars is limited. Shear movement of one bar pair (e.g., $120a_2$, $120b_2$) with respect to the opposite side bar pair (e.g., $120a_1$, $120b_1$) is controlled/limited by contact between the arm 138 and the side of the channel 172. As illustrated in FIGS. 8A-8C, the example threaded rod 170 can include two channels 172 (first channel 172a and second channel 172b). To prevent interference, the arms 138 extending from the upper bars $120a_1$, $120a_2$ engage opposite channels, e.g., the arm 138 extending from the first upper $120a_1$ bar can engage the first channel 172a and the arm extending from the second upper bar $120a_2$ can engage the second channel 172b. Likewise, the arms extending from the lower bars 120b can engage different channels, e.g., the arm extending from the first lower bar $120b_1$ can engage the second channel 172b and the arm extending from the second lower bar $120b_2$ can engage the first channel 172a. The upper and lower bars 120a, 120b can also include a recess 139 for receiving all or a portion of the arm 138 extending from the opposing upper/lower bar 120a, 120b. For example, as illustrated in FIGS. 8A and 8B, the first upper bar $120a_1$ can include a recess 139 for receiving a portion of the arm 138 extending from the second upper bar $120a_2$. Likewise, the second upper bar $120a_2$ can include a recess 139 for receiving a portion of the arm 138 extending from the first upper bar $120a_1$. The recess 139 allows the intervertebral cage 100 to have a smaller size when in an unexpanded configuration by allowing the arms 138 to overlap with each of the opposing bars 120. In an example cage 100, the recess 139 can define the limit of lateral movement between opposing bar pairs $120a_1$, $120b_1$ and $120a_2$, $120b_2$ towards each other. The arms 138 and corresponding recesses 139 can be located at any point along the length of the bar 120. As illustrated in FIGS. 8A-8C, the arms 138 and recesses 139 are located proximate the pin 150 location. It is contemplated, however, that the arms 138 and recesses 139 can be located proximate the ends of the bars 120. The arms 138 and recesses 139 can also be located at positions symmetrical or asymmetrical about the midline plane of the bars 120.

Figure 9A:
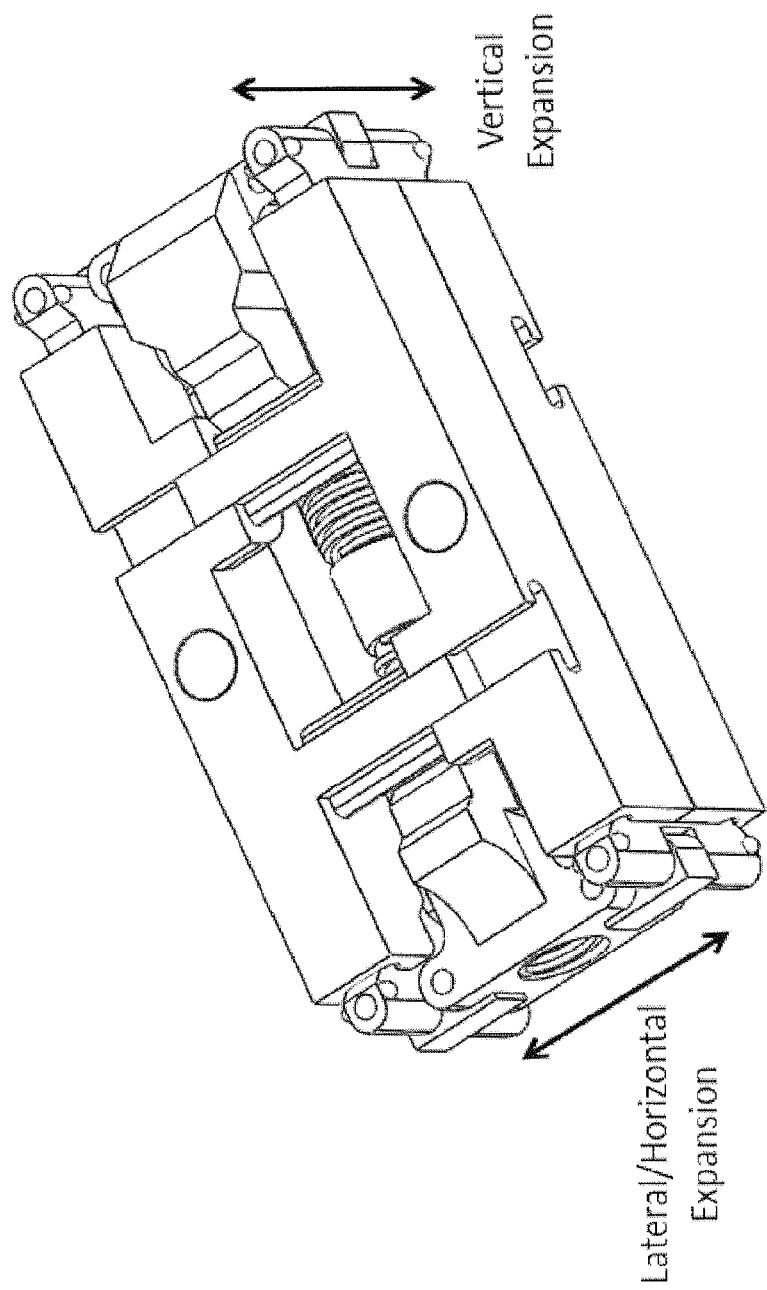
FIGS. 9A-9D are perspective views of an example intervertebral cage.
Figure 9B:
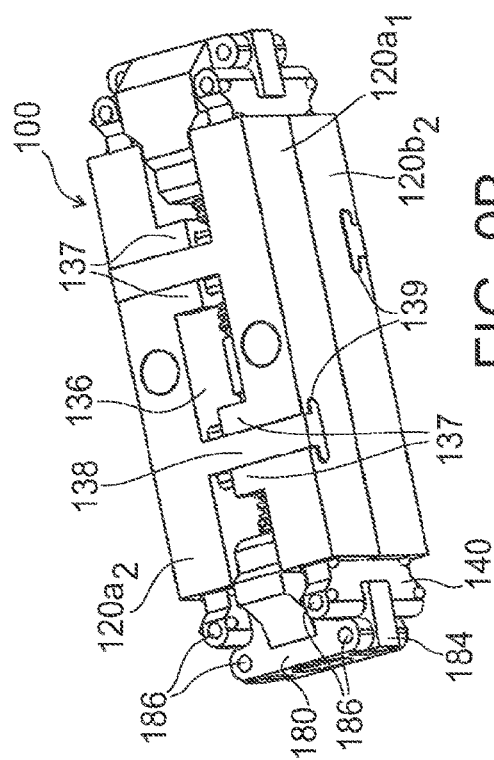
Figure 9D:
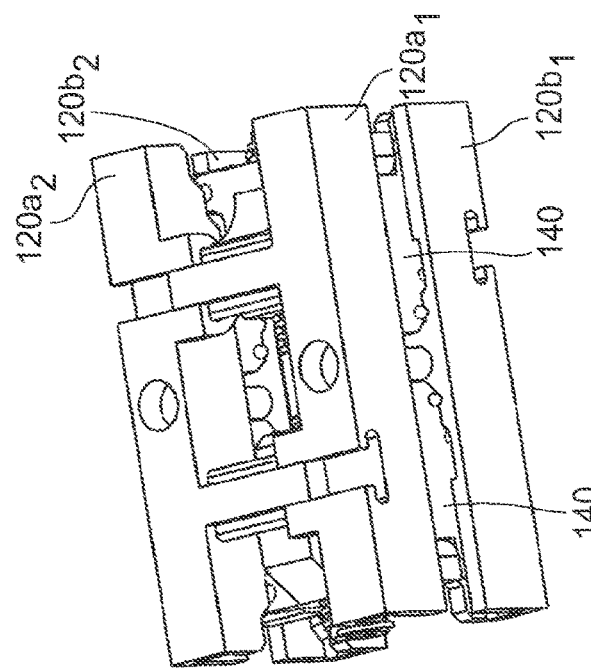
Figure 9C:
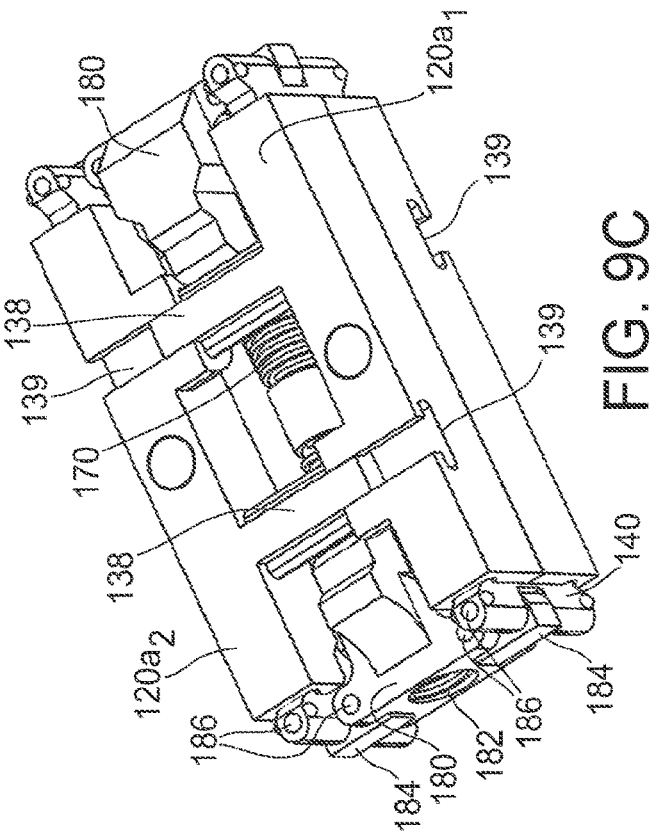

Expansion of the cage 100 will now be explained in reference to FIGS. 9A-9D. As outlined above, and illustrated in annotated FIG. 9A, the cage 100 can be expanded in both the lateral and vertical direction. Lateral and/or vertical expansion can be symmetrical or asymmetrical with respect to opposing bar pairs and/or opposite ends of the same bar pair. FIGS. 9B-9D are perspective views of the example intervertebral cage 100 in transition from an unexpanded configuration (FIG. 9B) to a lateral expanded configuration (FIG. C), to a fully expanded, lateral and vertical, configuration (FIG. 9D). Though not illustrated, asymmetrical expansion can be accomplished by including different height separators 140 between the opposing bar pairs $120a_1$, $120b_1$ and $120a_2$, $120b_2$. For example, the first bar pair $120a_1$, $120b_1$ can include a separator 140 having a first height and the second bar pair $120a_2$, $120b_2$ can include a separator 140 having a second/different height. Likewise, asymmetrical expansion can be accomplished by including opposing bar pairs $120a_1$, $120b_1$ and $120a_2$, $120b_2$ with different height. The example cage 100 includes a threaded rod 170 for controlling/limiting lateral movement between adjacent bar pairs $120a_1$, $120b_1$ and $120a_2$, $120b_2$. Each of the bars upper and lower bars 120a, 120b include an arm 138 for engaging all or a portion of the corresponding recess/channel 139 in the respective opposing bar pair. For example, as illustrated in FIGS. 9A-9D, the first upper bar $120a_1$ can include a recess 139 for receiving the arm 138 extending from the second upper bar $120a_2$. Likewise, the second upper bar $120a_2$ can include a recess 139 for receiving the arm 138 extending from the first upper bar $120a_1$. Similar arm 138/recess 139 configurations can be included on the first and second lower bar $120b_1$ and $120b_2$. Shear movement between the bar pairs $120a_1$, $120a_2$ and $120b_1$, $120b_2$ can be controlled/limited by contact between the arms 138 and the side walls of the recesses 139. In the example cage 100, the recess 139 can extend through the entire width of the bars 120. Each of the bars 120 can also include a projection 137 extending from the side surface 136 of the bar 120 in a direction towards the opposing upper/lower bar 120a, 120b. The projection 137 can allow the bar pairs $120a_1$, $120a_2$ and $120b_1$, $120b_2$ to be in contact once the intervertebral cage 100 is as it maximum horizontal expansion The projection 137 can also contact the threaded rod 170 and/or spacer 180 during lateral expansion. The projection 137 can be used to maintain connection between both sets of bars 120 after the cage 100 is fully laterally expanded, as illustrated in FIGS. 9C and 9D.

As outlined above, the bar pairs $120a_1$, $120b_1$ and $120a_2$, $120b_2$ are spaced from one another across the vertical midline of the cage 100. The space between the bar pairs $120a_1$, $120b_1$ and $120a_2$, $120b_2$ can be widened when the cage 100 is expanded in the horizontal/lateral and vertical direction. To cause movement of each bar pair $120a_1$, $120b_1$ and $120a_2$, $120b_2$ in the lateral and vertical direction the cage 100 includes at least one spacer 180 having a threaded opening 182 for engaging the threaded rod 170. The spacer 180 is coupled to the separator 140 via connectors 184 and pins 186, allowing the spacer 180 to pivot relative to each connector 184 and allowing the connectors 184 to pivot relative to the separator 140.

The spacer 180 is moveable along the threaded rod into and between the space between the bar pairs $120a_1$, $120b_1$ and $120a_2$, $120b_2$. To cause expansion, the threaded rod 170 engages the threads provided in the threaded opening 182 of the spacer 180 to move the spacer 180 into the space between the bar pairs $120a_1$, $120b_1$ and $120a_2$, $120b_2$. The spacers 180, for example, may be drawn to each other along the threaded rod 170 by having different direction threads within their respective openings 182. As the spacers 180 advance towards each other, the connectors 184 pivot relative to the spacers 180 and to the separators 140. This movement urges the bars 120 horizontally away from the midline plane of the cage 100 as provided in FIG. 9C, illustrating the cage 100 in a horizontally expanded configuration. Once horizontal expansion is complete, vertical expansion of the cage 100 is accomplished by further engagement between the threaded rod 170 engages the threads provided in the threaded opening 182 of the spacer 180. For example, the connectors 184 can pivot approximately 90° with respect to the spacers 180, further rotation of the threaded rod 170 results in vertical expansion of the cage 100/bars 120. As the spacer 180 advances on the threaded rod 170, the separator 140 is advanced along the contact surface 126 of the bar 120. FIG. 9D illustrates an example cage 100 after both horizontal and vertical expansion.

Figure 10A:
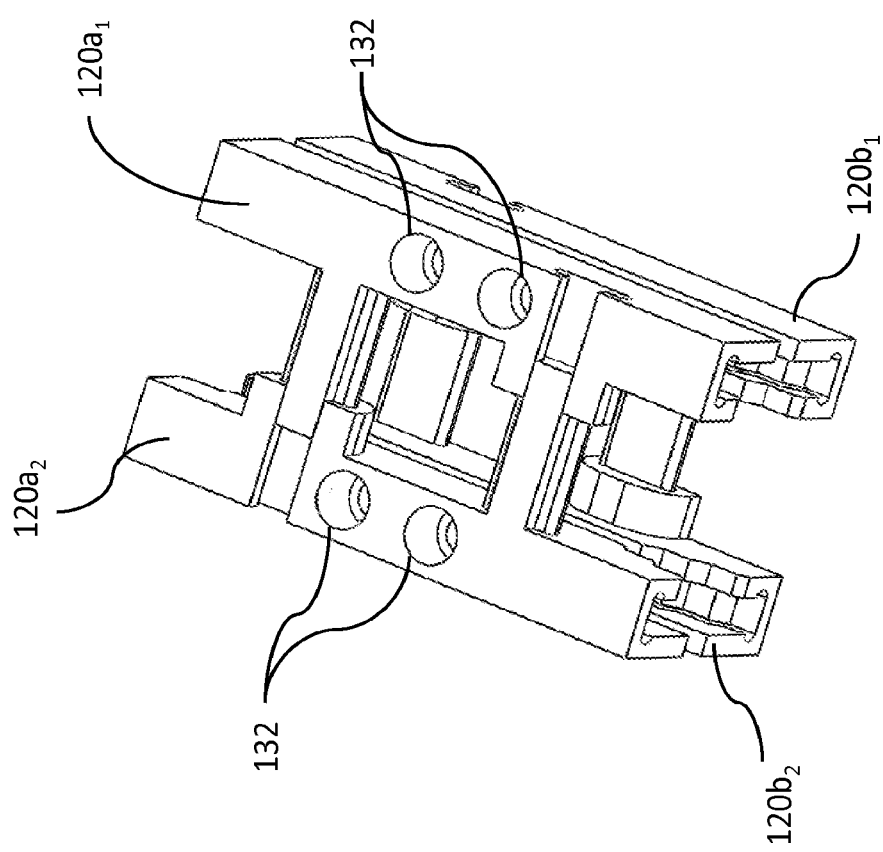
FIG. 10A is a perspective view of example upper and lower bar pairs of an intervertebral cage.
Figure 10B:
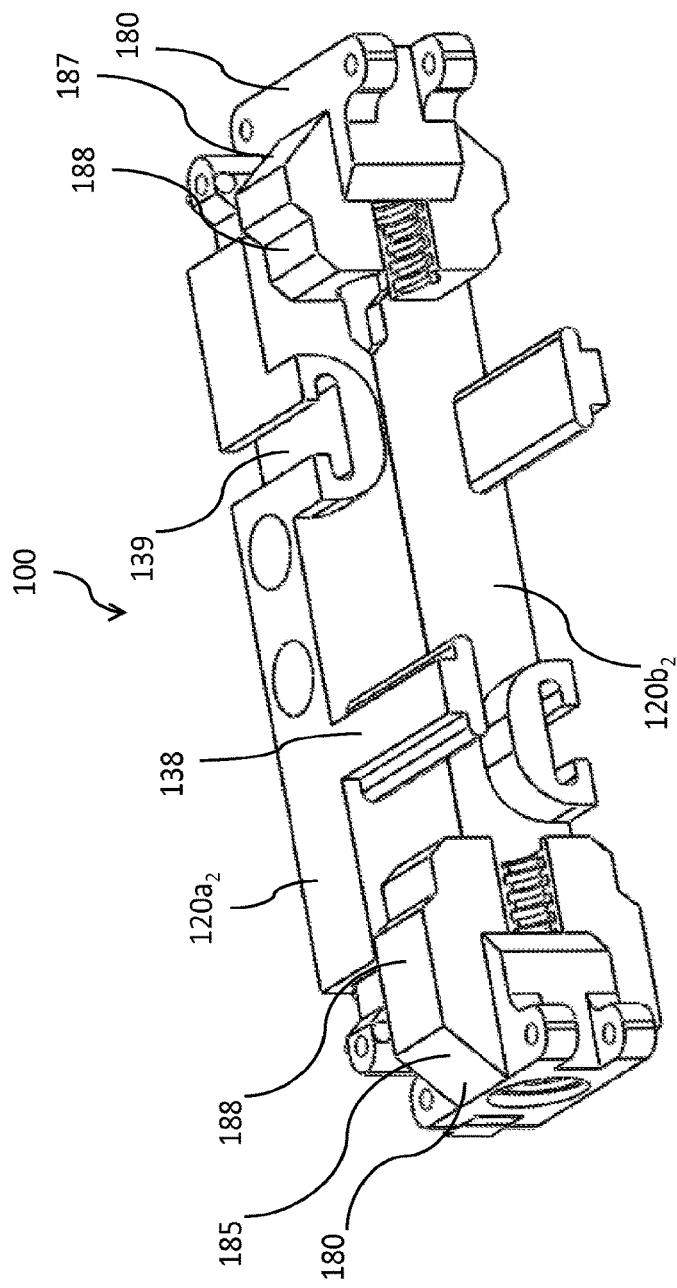
FIG. 10B is a cross-section of the example cage of FIG. 10A in an unexpanded configuration.
Figure 10C:
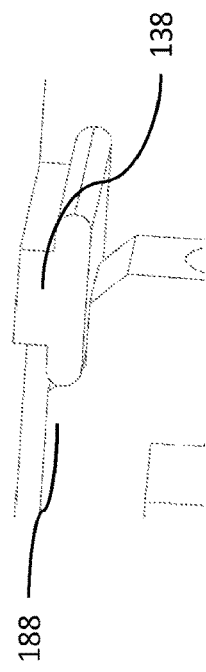
FIG. 10C is a partial cross-section of the example cage of FIG. 10A.
Figure 10D:
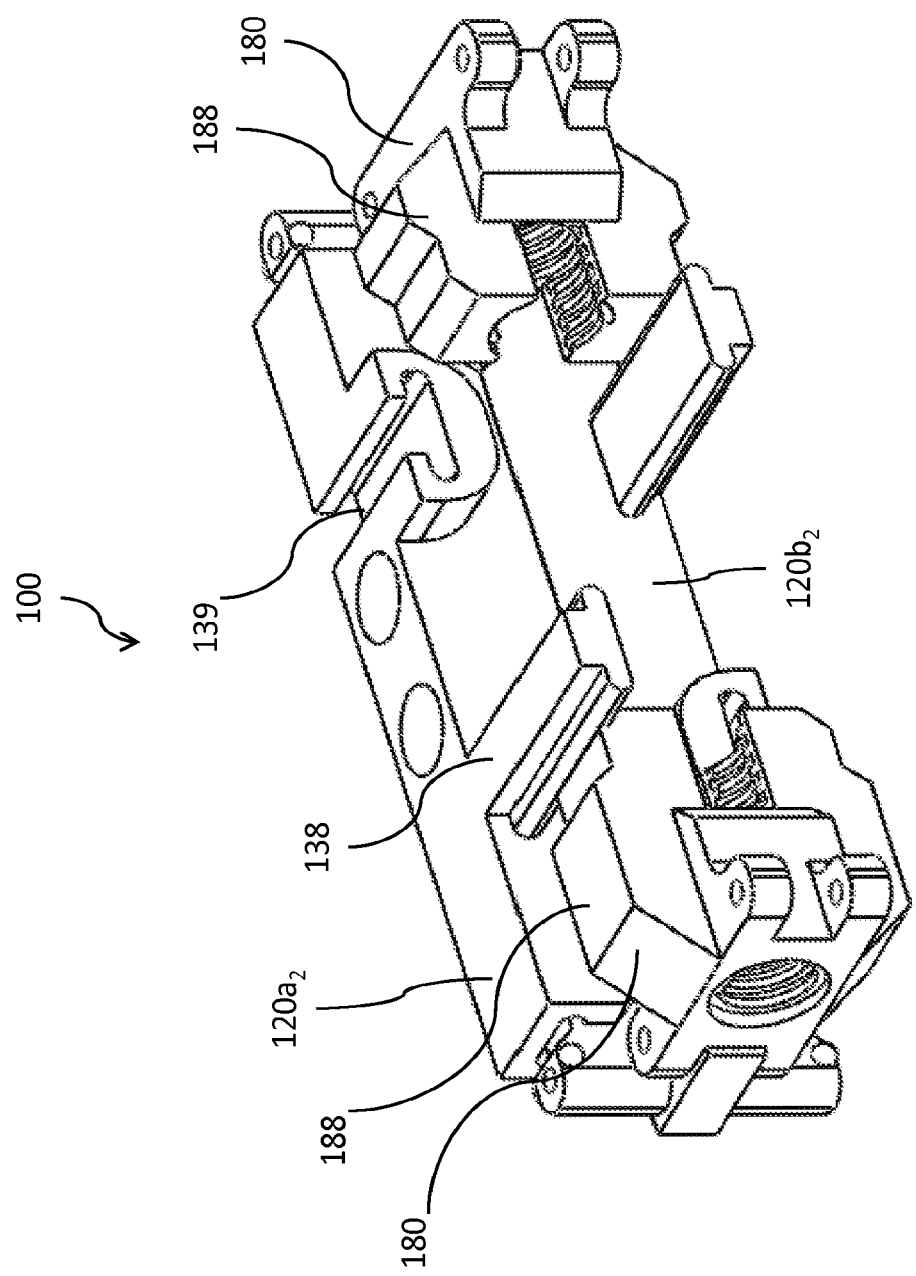
FIG. 10D is a perspective view of an example cage of FIG. 10A in a horizontally expanded configuration.
Figure 10E:
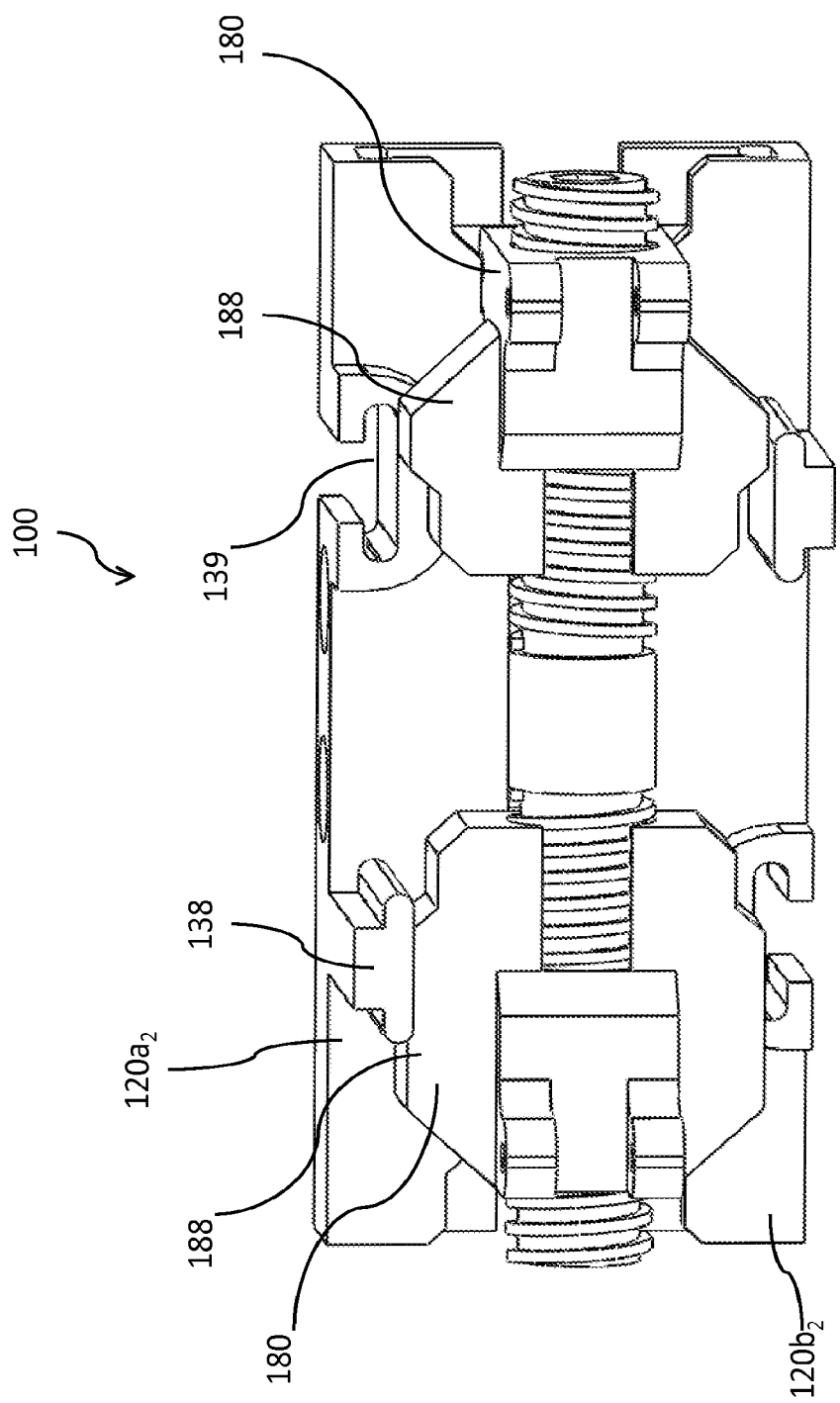
FIG. 10E is a cross-section of the example cage of FIG. 10A in a vertically and horizontally expanded configuration.

FIG. 10A is a perspective view of another example upper and lower bar pair $120a_1$, $120b_1$ and $120a_2$, $120b_2$ of an intervertebral cage 100. The cage 100 components illustrated in FIGS. 10A-10E includes similar components and function as that described in reference to FIGS. 9A-9D. As provided in FIG. 10A, cage 100 can include two openings 132 for pins 150 on the bars 120. FIGS. 10B-10D are cross-section views of the example cage 100. FIG. 10B provides the cage 100 in an unexpanded configuration. FIG. 10D provides the cage in a fully horizontal expanded configuration. FIG. 10E shows a perspective view of the cage 100 in a horizontally and vertically expanded configuration.

Cage 100 can include spacers 180. The spacers 180 can have varying external structure to facilitate insertion/implantation and/or fusion. For example, the spacer 180 can include a sloped leading surface 185 to facilitate insertion into the vertebral disc space and facilitate vertical expansion of the disc space. The sloped surface 185 can begin proximate the distal end of the spacer 180. Likewise, the spacer 180 located at the trailing end can include a sloped/curved surface 187 starting at position recessed from the leading edge for receiving bone filling material. The curved or sloped surface 187 can receive bone filling material. The curved/sloped surface 187 can also be used to guide bone filling material into the cage 100 when fully expanded.

The spacers 180 can also include a support portion 188 for providing support to the arms 138 extending from the upper and lower bars 120a, 120b. The support portion 188 can include a lower surface, an incline (that may mirror the incline of the separators 140) and an upper surface. The lower surface provides support to the arms 138 when the cage 100 is in an horizontally expanded configuration (FIG. 10D) and the upper surface provides support to the arms 138 when the cage 100 is in a fully (horizontally and vertically) expanded configuration (FIG. 10E).

Figure 12:
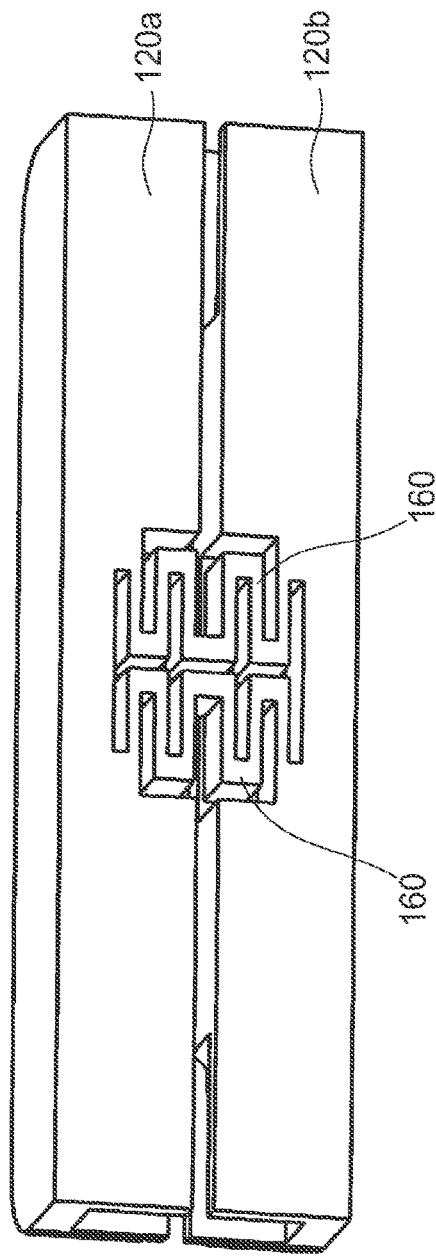
FIG. 12 is a perspective view of an example bar pair connected with a compliant mechanism.
Figure 13:
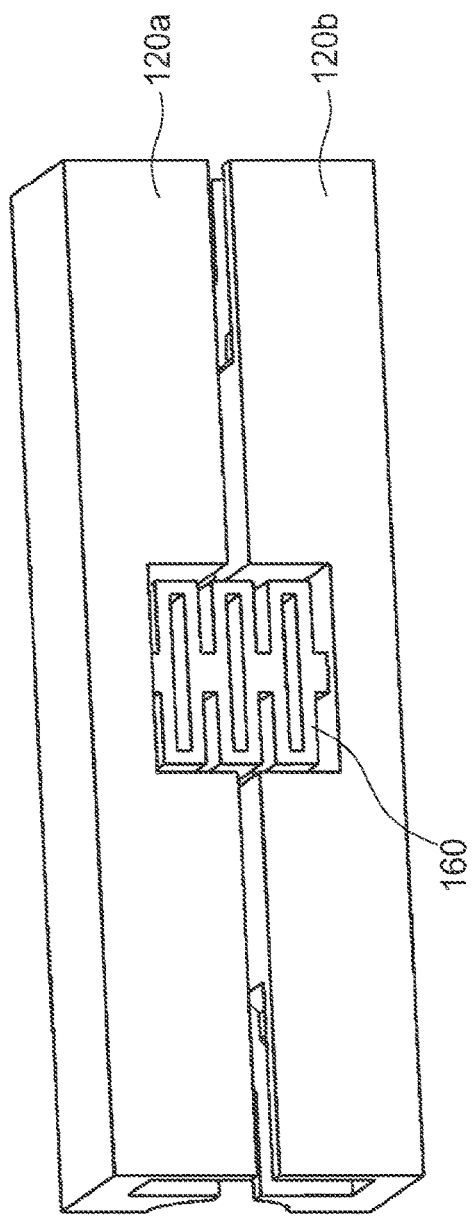
FIG. 13 is a perspective view of an example bar pair connected with a compliant mechanism.
Figure 14:
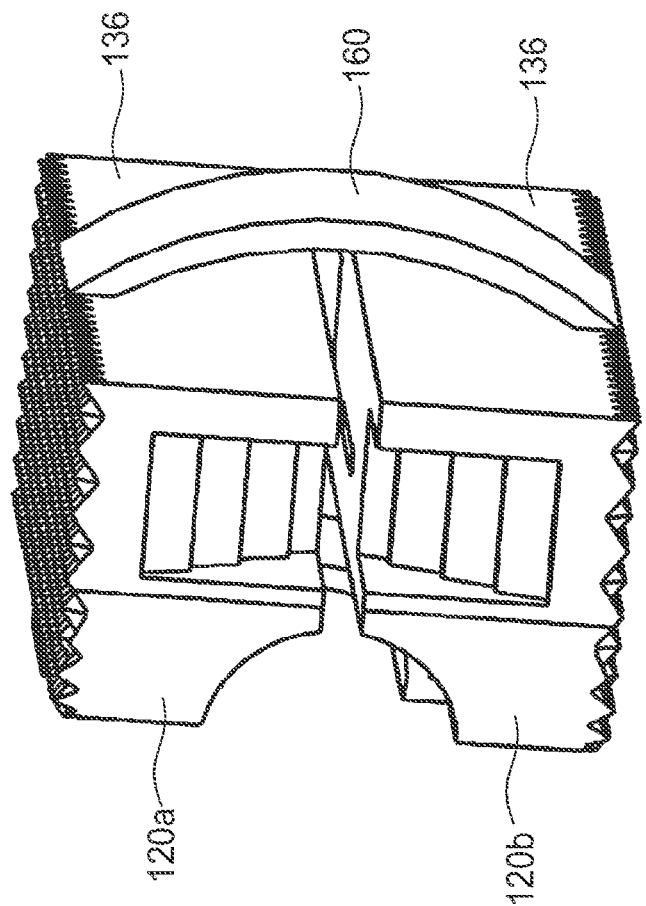
FIG. 14 is a perspective view of an example bar pair connected with a compliant mechanism.

As described above, a separator 140 can be used to define a distance/separation between the upper and lower bar pairs 120a, 120b and the height of the cage 100. In another example, illustrated in FIGS. 11-15, a compliant mechanism 160 can be used to control expansion and contraction of the upper and lower bars 120a, 120b. The compliant mechanism 160 can be used in conjunction with or exclusive from the separator 140 and/or pin 150. As the upper and lower bars 120a, 120b are compressed, the compliant member 160 acts as a spring providing a resistive force. In an example cage 100, the compliant mechanism 160 can be in equilibrium in the fully compressed state and accordingly provides resistive force during distraction of the compliant member 160/upper and lower bars 120a, 120b. The compliant member 160 can provide a constant resistive force in response to the distraction of the upper and lower bars 120a, 120b. In another example, the compliant member 160 can provide an irregular or phase resistive force in response to the distraction of the upper and lower bars 120a, 120b. FIGS. 11A and 11B show a front and perspective view of an example an upper and lower bar pair 120a, 120b including a round/circular-shaped compliant member 160. The round complaint member 160 can be formed integral to the upper and lower bars 120a, 120b. Distraction of the upper and lower bars 120a, 120b causes the compliant member 160 to deform within the opening provided in the bars 120. Distraction can be limited by the clearance provided between the compliant member 160 and the upper and lower bars 120a, 120b, that is, the distraction can be limited by contact of the compliant member 160 with the surface of the bar opening 162. Distraction can also be limited by modifying the stiffness of the compliant member 160. FIGS. 12 and 13 provide perspective views of an upper and lower bar pair 120a, 120b including additional examples of compliant members 160. In FIG. 12, the compliant member 160 includes two u-shaped or saddle shaped compliant members 160. In FIG. 13, the compliant member 160 includes a loop-shaped structure. In another example, illustrated in the perspective view of FIG. 14, the compliant member 160 can be coupled to the side surface 136 of the upper and lower bars 120a, 120b. For example, the compliant member 160 can include an arched structure coupled to the side of the bars and providing resistance against distraction of the upper and lower bars 120a, 120b.

Figure 15:
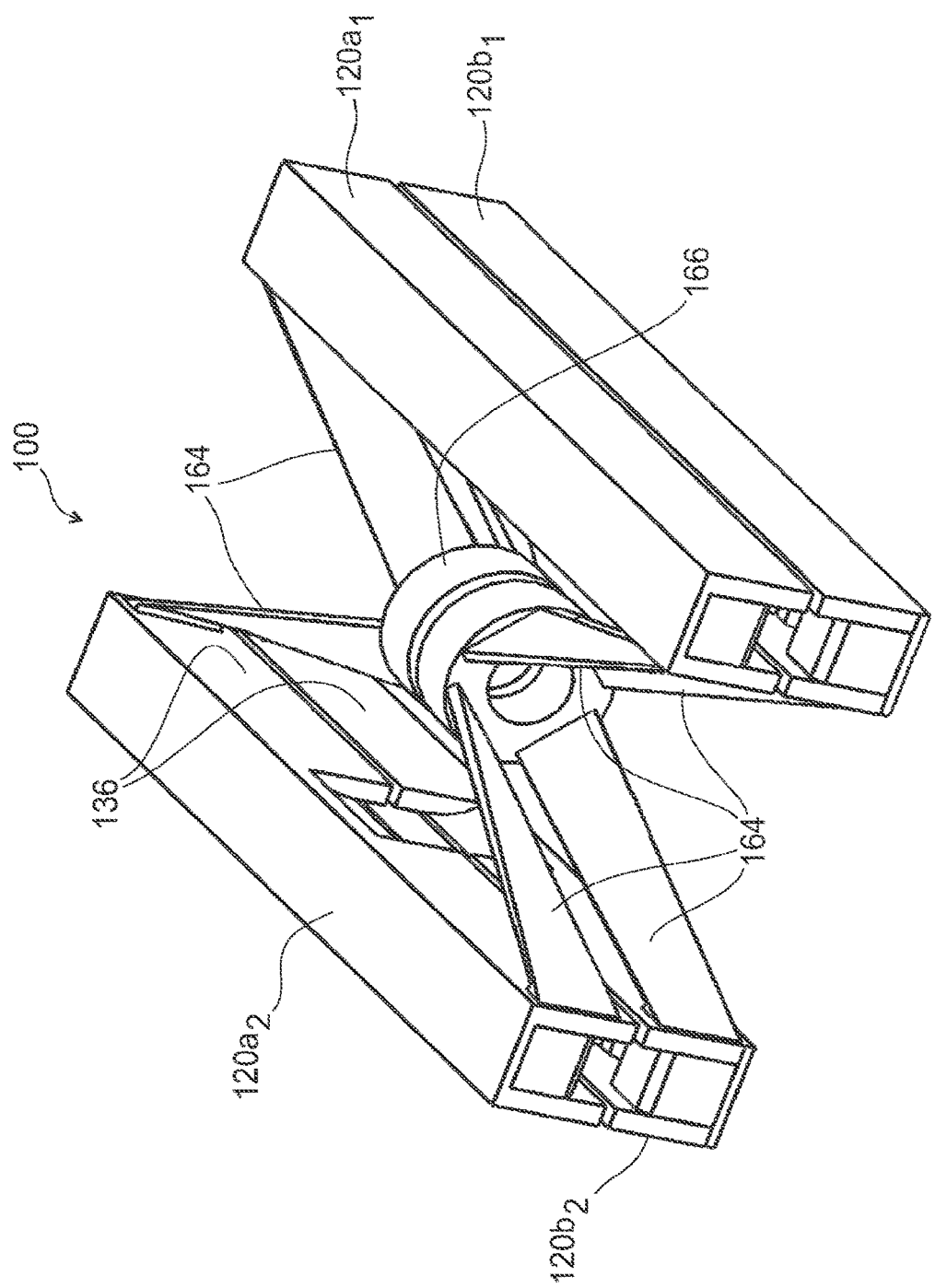
FIG. 15 is a perspective view of an example intervertebral cage connected with compliant mechanisms.

FIGS. 15, 16A and 16B are perspective views of an intervertebral cage 100. The cage 100 includes two upper and lower bar pairs $120a_1$, $120b_1$ and $120a_2$, $120b_2$, and a compliant member 160. The compliant member 160 can include ligaments/legs 164 extending from a center member 166 and coupled to a side surface 136 of the upper and lower bars $120a_1$, $120b_1$ and $120a_2$, $120b_2$. The ligaments 164 can provide a resistive force in both the vertical and lateral directions by providing tension between upper and lower bars pairs $120a_1$, $120b_1$ and $120a_2$, $120b_2$ and the center member. The center member 166 connects the ligaments 164 and can receive a (threaded) bar which can inhibit rotation of the upper and lower bar pairs $120a_1$, $120b_1$ and $120a_2$, $120b_2$ with respect to the center member 166, thereby limiting shearing (lateral movement) between the upper and lower bar pairs $120a_1$, $120b_1$ and $120a_2$, $120b_2$. As illustrated in FIGS. 16A and 16B, the upper and lower bars $120a_1$, $120b_1$ and $120a_2$, $120b_2$ can include an arm 122 extending from the top surface 124 of each of the bars 120. The arm 122 can be used to provide stability to the coupled upper and lower bar pair $120a_1$, $120b_1$ and $120a_2$, $120b_2$. The arms 122 can be used maintain the bar pairs in a parallel configuration. For example, the arms 122 can include a bottom projection/lip 123 that engages the center member 166 of the compliant mechanism 160. This engagement can be used to maintain a parallel relationship between the bar pairs $120a_1$, $120b_1$ and $120a_2$, $120b_2$ and further limit rotational movement of the cage 100. The arms 122 can be constructed from a rigid, semi-rigid or compliant material. In one example, the arms 120 can bend or deform to accommodate the endplate of the adjacent vertebral body.

Figure 17C:
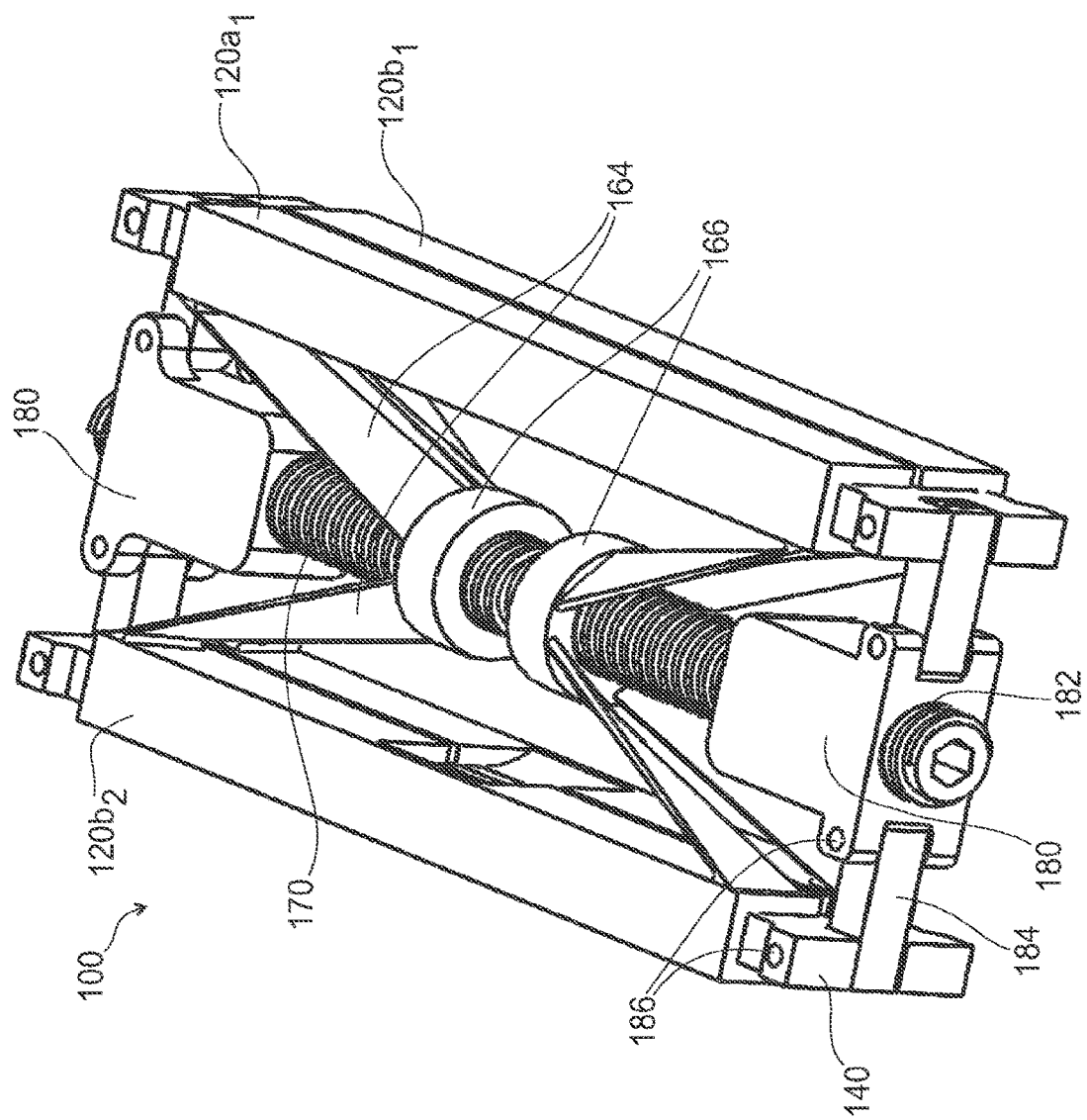

FIGS. 17A-17C provide another example intervertebral cage 100 including a threaded rod 170 and a compliant member 160 for controlling/limiting lateral movement between adjacent bar pairs. The example cage 100 can include two upper and lower bar pairs (each pair including an upper bar and a lower bar) $120a_1$, $120b_1$ and $120a_2$, $120b_2$, a threaded rod 170 extending between the bar pairs along the midline of the cage 100, spacers 180 operatively coupled to the threaded rod 170 and the bar pairs $120a_1$, $120b_1$ and $120a_2$, $120b_2$ via connectors 184. The example cage 100 can also include two compliant members 160 having ligaments/legs 164 extending from a center member 166 and coupled to a side surface 136 of the upper and lower bars 120a, 120b. The ligaments 164 can provide a resistive force in both the vertical and lateral directions by providing tension between upper and lower bars pairs $120a_1$, $120b_1$ and $120a_2$, $120b_2$ and the center members 166. The center member 166 connects the ligaments 164 and can receive a partial or fully threaded bar 182 which can inhibit rotation of the upper and lower bar pairs $120a_1$, $120b_1$ and $120a_2$, $120b_2$ with respect to the center members 166 and each other, thereby limiting shearing (lateral movement) between the upper and lower bar pairs $120a_1$, $120b_1$ and $120a_2$, $120b_2$. The bar pairs $120a_1$, $120b_1$ and $120a_2$, $120b_2$ are spaced from one another across the vertical midline of the cage 100. The space between the bar pairs $120a_1$, $120b_1$ and $120a_2$, $120b_2$ can be widened when the cage 100 is expanded in the horizontal and vertical direction by rotation of the threaded shaft 170 and engagement of the spacers 180 and separators 140, as outlined above.

FIGS. 18A-18K provide another example cage 200. Similar to cage 100 described above, cage 200 is designed for implantation and fusion between adjacent vertebrae. It is contemplated that cage 100 and cage 200 may include like components. Where possible, corresponding element numbers are used to describe like components.

As will be described in more detail below, cage 200 can expand horizontally and/or vertically. For example, once positioned the cage 200 can be expanded in a horizontal direction in the plane of the intervertebral space in which the cage 200 is located. The cage 200 can also be expanded in a vertical direction to increase the vertical separation between the adjacent vertebrae. A single actuator, or plurality of actuating devices, can be used to provide horizontal and vertical expansion.

The cage 200 can include a pair of front and back lateral bars 210a, 210b and a pair of upper and lower horizontal bars 220a, 220b. The lateral and horizontal bars surround a central component 240. The cage 200 can include a plurality of actuating members, for example, threaded rod 270 and screws 275. The threaded rod 270 and screws 275 can be used to drive the expandable surfaces (lateral and horizontal bars 210, 220) of the cage 200.

As will be described in more detail below, the lateral and vertical space between the lateral and horizontal bars 210, 220 can be increased/decreased as the cage 200 is expanded/retracted. FIG. 18A is a perspective view of the cage 200 in an unexpanded configuration. FIG. 18B is a perspective view of the cage 200 in a horizontally expanded configuration. FIG. 18C is a perspective view of the cage 200 in a fully expanded (horizontal and vertical) configuration.

Figure 18D:
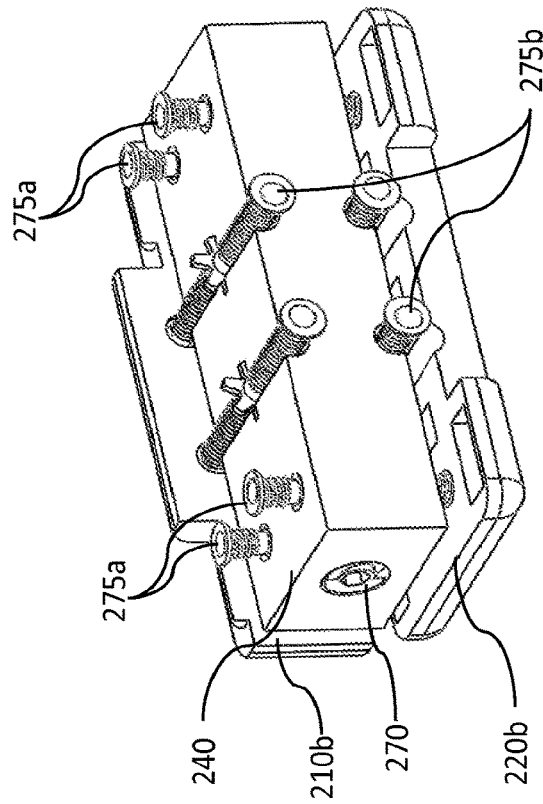
FIG. 18D is a perspective view of a lateral and a horizontal bar, central component, and actuating members.
Figure 18E:
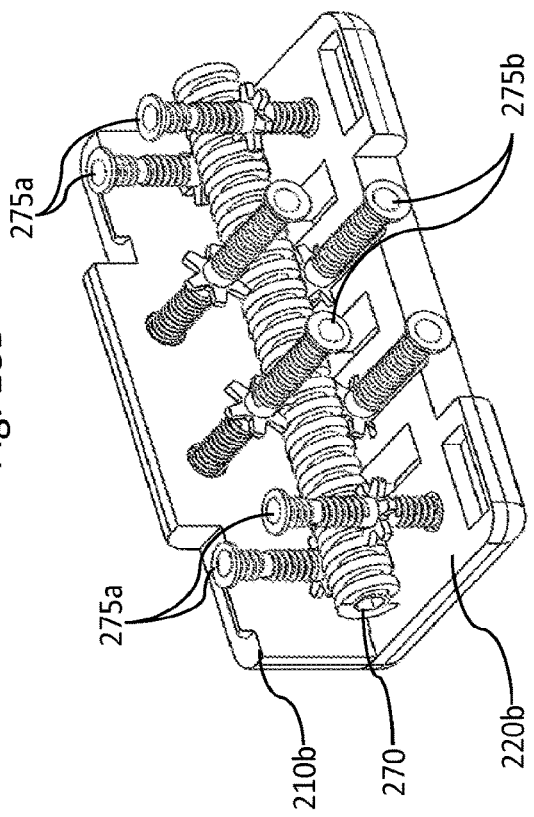
FIG. 18E is a perspective view of a lateral and a horizontal bar and actuating members.

FIGS. 18D-18G provide perspective views of various cage 200 components. As illustrated, the threaded rod 270 can extend through a bore provided in the central component 240. The bore can include a threaded or non-threaded interior surface. The screws 275 can extend through bores and/or channels provided in the central component 240. For example, as illustrated in FIG. 18D, vertical screws 275a can extend through bores extending between the top and bottom surface of the central component 240. Likewise, horizontal screws 275b can extend through horizontal channels/openings extending between the front and back side surfaces of the central component 240. The central component 240 can have braces extending from the horizontal/lateral surface to maintain the distance between the screws 275 and the central component 240. As provided in FIGS. 18E, 18G and 18H, screws 275 can movably engage the threaded rod 270 in an orthogonal arrangement. For example, screws 275 and threaded rod 270 can form a worm drive. In an example cage 200, the threads of the threaded rod 270 engage corresponding gears and/or threads of the screws 275. Each of the vertical screws 275a and horizontal screws 275b can engage and rotate with the threaded rod 270.

As illustrated in FIGS. 18A-18E, the screws 275 extend through the central component 240 and engage the lateral and horizontal bars 210, 220. For example, the vertical screws 275a engage the top and bottom horizontal bars 220a, 220b. Likewise, the horizontal screws 275b engage the front and back lateral bars 210a, 210b. The screws 275 can engage the lateral and horizontal bars 210, 220 via a threaded connection provided in the corresponding lateral or horizontal bar 210, 220. Rotation of the screws 275 can result in translation of the corresponding lateral or horizontal bar 210, 220. Screws 275 can include a head/lip for limiting motion between corresponding lateral or horizontal bar 210, 220. As provided in FIGS. 18A and 18B, the bores provided in the lateral and horizontal bars 210, 220 can include a counter bore/recess sized to accommodate the head/lip of the screw 275.

The cage 200 can be expanded horizontally and/or vertically. As outlined above, it is contemplated that the cage 200 is expanded horizontally, followed by vertical expansion. FIGS. 18B and 18I illustrate cage 200 in horizontally expanded configuration. To ensure that horizontal expansion occurs before vertical expansion, the top and bottom horizontal bars 220a, 220b do not contact the threaded portions of the vertical screws 275a. Accordingly, vertical expansion of the cage 200 will not occur until contact between the vertical screws 275a and the top and bottom horizontal bars 220a, 220b. FIG. 18J illustrates the cage 200 in an almost complete horizontally expanded configuration. As provided in FIG. 18J, the inside surface of the lateral bars 210 can include a lip/protrusion 212 for engaging a corresponding beveled edge 222 included on an inside surface of the horizontal bars 220. Engagement between the lip 212 and edge 222 can cause articulation between the lateral bars 210 and horizontal bars 220. That is, engagement between the lip 212 and edge 222 directs the upper and lower horizontal bars 220a, 220b vertically, thereby causing the upper and lower horizontal bars 220a, 220b to engage the vertical screws 275a.

Once the horizontal expansion of the front and back lateral bars 201a, 210b is complete, the vertical screws 275a engage the upper and lower horizontal bars 220a, 220b. Additional rotation of the threaded rod 270 results in vertical expansion/separation of the upper and lower horizontal bars 220a, 220b. To inhibit excess lateral expansion, while vertical expansion is occurring, the ends of horizontal screws 275b do not include threads. Accordingly, only vertical expansion occurs at the end phase of the cage 200 expansion. FIG. 18K illustrates the cage 200 in a vertically and horizontally expanded configuration.

The cage 200 can include surface features, treatment and/or recesses to encourage fusion between the cage 200 and the adjacent vertebral bodies. As illustrated in FIGS. 18A-18C, the lateral bars 210 and/or horizontal bars 220 can include rectangular openings 224 to receive bone filing material/biologics. The openings 224 can also permit the worm/gears associated with the screws 275 to rotate without impacting or otherwise damaging the lateral and/or horizontal bars 210, 220.

One or more components of the cage 100/200 may be made from any biocompatible material known including, for example, metals such as titanium, titanium alloys, stainless steel and cobalt chromium. Other materials include, for example, composites, polymers, ceramics, bone (allograft) and any other materials suitable for the cage 100/200. In one example, the cage 100/200 can be constructed from a radiopaque material including, for example, stainless steel such as 17-4PH stainless steel. Likewise, one or more components of the cage 100/200 can be constructed from a radiolucent material to enhance visibility of the assembly during radiographic imaging. Example radiolucent materials can include "life science" grade PEEK (Ketron 450G PEEK). Life science grade PEEK can improve wear and abrasion characteristics as well as provide high yield strength.

While the foregoing description and drawings represent the an example implementation of the present invention, it will be understood that various additions, modifications, combinations and/or substitutions may be made therein without departing from the spirit and scope of the present invention as defined in the accompanying claims. In particular, it will be clear to those skilled in the art that the present invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. In addition, features described herein may be used singularly or in combination with other features. The presently disclosed embodiments are, therefore, to be considered in all respects as illustrative and not restrictive, the scope of the invention being indicated by the appended claims and not limited to the foregoing description.

It will be appreciated by those skilled in the art that changes could be made to the example implementations described above without departing from the broad inventive concept thereof. It is understood, therefore, that this invention is not limited to the particular examples disclosed, but it is intended to cover modifications within the spirit and scope of the present invention, as defined by the following claims.

What is claimed is:

1. An intervertebral cage comprising:
   a first support member including an upper contact surface and an opposing lower contact surface;
   a second support member laterally spaced from the first support member, the second support member including an upper contact surface and an opposing lower contact surface;
   a spacer extending between the first support member and the second support member, the spacer pivotably coupled to a longitudinal end of the first support member and a longitudinal end of the second support member; and
   a drive mechanism for driving movement of the spacer, wherein pivotable engagement between the spacer and first and second support members directs lateral movement between the first and second support members.

2. The intervertebral cage of claim 1, wherein engagement between the drive mechanism and the spacer directs movement of the spacer along a longitudinal axis of the drive mechanism, the longitudinal axis of the drive mechanism extending perpendicular to a direction of the lateral movement of the first and second support members.

3. The intervertebral cage of claim 2, wherein the spacer moves longitudinally towards a midline of the intervertebral cage during lateral expansion of the first and second support members.

4. The intervertebral cage of claim 2, wherein the spacer moves into a space between the first and second support members during lateral expansion of the first and second support members.

5. The intervertebral cage of claim 1, wherein the spacer includes a top surface,
   wherein the top surface of the spacer is coplanar with the upper contact surface of at least one of the first and second support members.

6. The intervertebral cage of claim 1, wherein the spacer includes a sloped leading surface to facilitate insertion into a vertebral disc space.

7. The intervertebral cage of claim 1, including a second spacer coupled to and extending between the first and second support members, the second spacer provided at an opposite longitudinal end of the intervertebral cage from the spacer,
   wherein engagement between the second spacer and first and second support members directs lateral movement of first and second support members.

8. The intervertebral cage of claim 7, wherein the second spacer includes a sloped trailing surface.

9. The intervertebral cage of claim 1, wherein rotational movement of the drive mechanism directs movement of the spacer into engagement with the first and second support members.

10. The intervertebral cage of claim 1, wherein the drive mechanism comprises a threaded rod.

11. The intervertebral cage of claim 10, wherein the spacer includes a threaded opening for engaging the threaded rod.

12. The intervertebral cage of claim 1, wherein the drive mechanism comprises a telescoping rod.

13. The intervertebral cage of claim 1, wherein the spacer is coupled to the first and second support members via pins that allow the spacer to pivot relative to each of the first and second support members.

14. The intervertebral cage of claim 13, wherein the first and second support members each include an arm extending from an end surface of a respective support member, each arm including an opening for engaging a respective pin.

15. The intervertebral cage of claim 1, wherein the upper and lower contact surfaces of each of the first and second support members have a shape corresponding to a shape of a vertebral endplate.

16. The intervertebral cage of claim 1, wherein the first and second support members include teeth extending from each of the respective upper and lower contact surfaces for providing engagement between the support members and adjacent vertebral bodies.

17. The intervertebral cage of claim 1, wherein the first support member comprises a first upper bar and an opposing first lower bar and the second support member comprises a second upper bar and an opposing second lower bar,
   wherein movement of the spacer along a longitudinal axis of the drive mechanism directs vertical movement between the first upper and lower bars and a corresponding vertical movement between the second upper and lower bars.

18. The intervertebral cage of claim 17, wherein engagement between the spacer and the first and second support members directs lateral movement of the first and second support members prior to directing vertical movement of the first upper and lower bars and the second upper and lower bars.

19. The intervertebral cage of claim 17, wherein the spacer includes a first separator movable between the first upper and lower bars of the first support member to direct vertical movement therebetween,
   wherein the spacer includes a second separator movable between the second upper and lower bars of the second support member to direct vertical movement therebetween.

20. The intervertebral cage of claim 19, wherein the first and second separators include a ramped surface for engaging a corresponding ramped surface provided on at least one of the first upper and lower bars and at least one of the second upper and lower bars, respectively.

* * * * *